(12) United States Patent
Dixson et al.

(10) Patent No.: US 8,193,118 B2
(45) Date of Patent: Jun. 5, 2012

(54) INSECTICIDAL SUBSTITUTED BENZYLAMINO HETEROCYCLIC AND HETEROARYL DERIVATIVES

(75) Inventors: John A. Dixson, Spearfish, SD (US); George Theodoridis, Princeton, NJ (US); Zeinab M. Elshenawy, Holland, PA (US); Benjamin J. Dugan, Glen Mills, PA (US); Manorama M. Patel, West Windsor, NJ (US); Edward J. Barron, Trenton, NJ (US); Stephen F. Donovan, Revere, PA (US)

(73) Assignee: FMC Corporation, Philadelphia, PA (US)

( * ) Notice: Subject to any disclaimer, the term of this patent is extended or adjusted under 35 U.S.C. 154(b) by 938 days.

(21) Appl. No.: 11/914,526

(22) PCT Filed: May 19, 2006

(86) PCT No.: PCT/US2006/019365
§ 371 (c)(1),
(2), (4) Date: Sep. 10, 2008

(87) PCT Pub. No.: WO2006/127426
PCT Pub. Date: Nov. 30, 2006

(65) Prior Publication Data
US 2009/0036306 A1 Feb. 5, 2009

Related U.S. Application Data

(60) Provisional application No. 60/682,460, filed on May 19, 2005.

(51) Int. Cl.
*A01N 57/00* (2006.01)
*A01N 43/76* (2006.01)
*A01N 43/50* (2006.01)
*A01P 7/04* (2006.01)
*A01P 21/00* (2006.01)

(52) U.S. Cl. .......... 504/101; 504/128; 504/138; 514/92; 514/377

(58) Field of Classification Search .................. 514/370
See application file for complete search history.

(56) References Cited

U.S. PATENT DOCUMENTS

| 4,195,092 A | 3/1980 | Balko |
| 4,256,755 A * | 3/1981 | Smith, Jr. ...................... 514/377 |
| 6,462,049 B1 | 10/2002 | Ogura et al. |
| 6,875,768 B1 | 4/2005 | Machiya et al. |

FOREIGN PATENT DOCUMENTS

| FR | 1313055 | * | 12/1962 |
| WO | WO 91/05473 A1 | | 5/1991 |
| WO | WO2005/063724 | * | 7/2005 |

OTHER PUBLICATIONS

Jennings, K. R. et. al. Pesticide Biochemistry and Physiology, 1988, v. 30, p. 190-197.*

Hirashima, A. et. al. Chemistry & Biodiversity, 2004, v. 1, issue 11, p. 1652-1667.*

Hirashima, A. et al. Pesticide Biochemistry and Physiology, 1997, v. 58, pp. 219-228.*

Hirashima, A. et al. Journal of Pesticide Science, 1996, v. 21, pp. 419-424.*

English Machine translation of FR1313055, published 1962.*

Hirashima, A., et al., "Quantitative structure-activity studies of octopaminergic ligands against *Locusta migratoria* and *Periplaneta americana*," *Pestic. Sci.* 55:119-128, Society of Chemical Industry, Wiley & Sons, England (1999).

Hirashima, A., et al., "Quantitative Structure-Activity Studies of Some Octopaminergic Agonists against *Periplaneta americana*," *Pestic. Sci.* 43:311-315, SCI, Wiley & Sons, Great Britain (1995).

Hirashima, A., et al., "Synthesis and Octopaminergic Agonist Activity of 2-(Substituted benzylamino)-2-thiazolines," *Biosci. Biotech. Biochem.* 56:1062-1065-1065, Japan Society for Bioscience, Biotechnology, and Agrochemistry, Japan (1992).

Reiter, J., et al., "Synthesis of new 'benzyl'-thiourea derivatives and their cyclic analogues with diuretic and saluretic activity," *Eur. J. Med. Chem.* 15:41-53, Chimica Therapeutica, Editions Scientifiques Elsevier, France (1980).

Oszczapowicz-B., I., and Oszczapowicz, J., "Detection and determination of imidic acid derivatives," in *The Chemistry of Functional Groups: Amidines*, vol. 2,259-262, Patai, S., ed., pp. 259-262, John Wiley & Sons, Chichester, England (1991).

International Search Report for International Application No. PCT/US06/19365, United States Patent and Trademark Office, Alexandria, Virginia, mailed on Aug. 20, 2007.

Hirashima, A. et al., "Inhibitors of calling behavior of *Plodia interpunctella*," *J. Insect Sci.(Online)* 3:1-9, University of Wisconsin Library (2003).

* cited by examiner

*Primary Examiner* — Mina Haghighatian
*Assistant Examiner* — Erin Hirt
(74) *Attorney, Agent, or Firm* — FMC Corporation

(57) ABSTRACT

Certain substituted benzylamino heterocyclic and heteroaryl derivatives have provided unexpected insecticidal and acaricidal activity. These compounds are represented by formula (I): wherein R, R1, R2, R3, and R4 are fully described herein. In addition, compositions comprising an insecticidally effective amount of at least one compound of formula (I), and optionally, an effective amount of at least one of an additional compound, with at least one insecticidally compatible carrier are also disclosed; along with methods of controlling insects comprising applying said compositions to a locus where insects are present or are expected to be present.

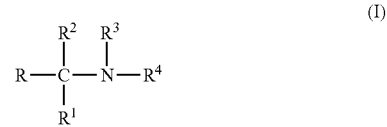

5 Claims, No Drawings

INSECTICIDAL SUBSTITUTED BENZYLAMINO HETEROCYCLIC AND HETEROARYL DERIVATIVES

This application claims the benefit of U.S. Provisional Application No. 60/682,460 filed May 19, 2005.

FIELD OF THE INVENTION

The present invention generally relates to pesticidal compounds and their use in controlling insects and acarids. In particular, it pertains to compositions of pesticidal substituted benzylamino heterocyclic and heteroaryl derivatives and agriculturally acceptable salts thereof, and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structure. Although there are many orders of insects that can cause significant crop damage, insects, for example, of the order "Homoptera" are of major importance. The order Homoptera includes, for example, aphids, leafhoppers, cicadas, whiteflies, and mealybugs. Homoptera have piercing/sucking mouthparts, enabling them to feed by withdrawing sap from vascular plants. Insect damage from Homoptera is manifested in several different ways, other than damage caused by direct feeding. For example, many species excrete honeydew, a sticky waste product that adheres to plants upon which the insect feeds and lives. Honeydew alone causes cosmetic injury to crop plants. Sooty molds will often grow on honeydew, making food products or ornamental plants look unappealing, thereby reducing their cosmetic and economic value. Some Homoptera have toxic saliva that is injected into plants while they are feeding. The saliva can cause plant damage through disfigurement and in some instances plant death. Homoptera can also vector disease-causing pathogens. Unlike direct damage, it does not take a large number of disease-vectoring insects to cause considerable damage to crop plants.

Thus, there is a continuing demand for new insecticides, and for new acaricides that are safer, more effective, and less costly. Insecticides and acaricides are useful for controlling insects and acarids which may otherwise cause significant damage both above and below the soil level to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of articles and patents disclose some substituted benzylamino heterocyclic and heteroaryl compounds that are reported to have pesticidal uses. For example, the Journal of Insect Science, 3:4 (available online: insectscience.org/3.4) reports the effectiveness of some octopamine agonists to suppress the calling behavior of the Indian meal moth, *Plodia interpunctella*. Included in the studies are compounds of the following structure:

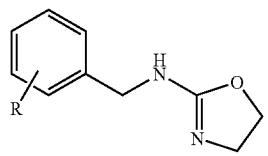

wherein
R is alkyl or two halogen atoms.

Pesticide Science, 55:119-128 (1999), describes the quantitative structure-activity studies of octopaminergic ligands against the migratory locust, *Locusta migratoria* and the American cockroach, *Periplaneta Americana*. Included in the studies are compounds of the formulae:

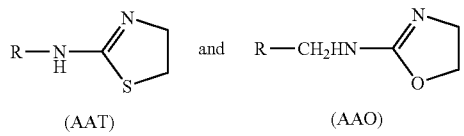

in which
R for formula (AAT) includes benzyl, and benzyl substituted with methyl, trifluoromethyl or one to two halogen atoms, and R for formula (AAO) includes phenyl substituted with trifluoromethyl or one to two halogen atoms.

Pesticide Science, 1995, 43 311-315 describes the quantitative structure-activity studies of some octopaminergic agonists against *Periplaneta Americana*. Included in the studies are compounds of the formula:

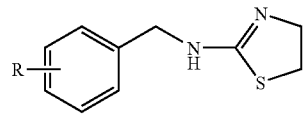

wherein
R is hydrogen, methyl, trifluoromethyl, methoxy or one to two halogen atoms.

Bioscience, Biotechnology, and Biochemistry (1992), 56(7), 1062-5 describes the synthesis and octopaminergic activity of 2-(substituted benzylamino)-2-thiazolines.

European Journal of Medicinal Chemistry (1980), 15(1), 41-53, describes the synthesis of new "benzyl"-thiourea derivatives and their cyclic analogs with diuretic and saluretic activity.

U.S. Pat. No. 4,195,092 discloses 2-(substituted amino)-N-(3-substituted phenyl)-2-imidazoline-1-carbothioamides, useful as insecticides, of the following formula:

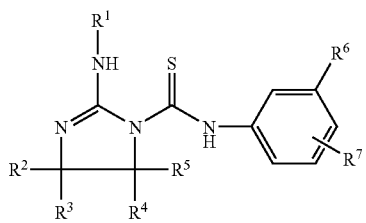

wherein
$R^1$ includes phenylalkyl, containing no more than about 18 carbon atoms, in which the phenyl moiety is optionally substituted with from one to three groups selected from $C_1$-$C_6$ alkyl, $C_1$-$C_6$ alkoxy, $C_1$-$C_6$ alkylthio, trifluoromethyl, halo, and cyano;

$R^2$, $R^3$, $R^4$, and $R^5$ independently are selected from hydrogen, $C_1$-$C_3$ alkyl, and phenyl;

$R^6$ represents halo, trifluoromethyl, cyano, or 1,1,2,2-tetrafluoroethoxy;

$R^7$ represents hydrogen, $C_1$-$C_3$ alkyl, or halo.

International Publication Number WO 91/05473 discloses fungicidal compositions, compounds, and their production and use of the following formulae:

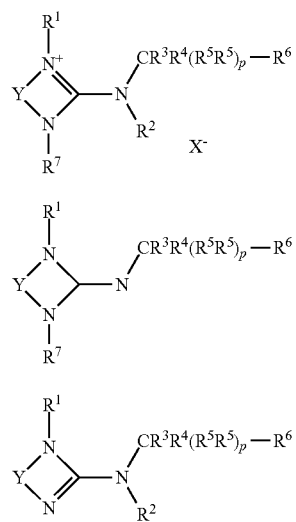

wherein
$R^1$ and $R^7$ are each independently hydrogen or $C_1$-$C_3$ allyl, $R^2$ is hydrogen or $C_1$-$C_6$ alkyl, $R^3$ and $R^4$ independently, and each $R^5$ independently are hydrogen or $C_1$-$C_4$ alkyl, $R^6$ is a cyclohexyl group or a monocyclic or bicyclic aromatic group, substituted with from 1 to 5 groups of the formula $R^8$, wherein $R^8$ is halogen, a $C_1$-$C_{10}$ alkyl group, a $C_1$-$C_{10}$ alkoxy group, a tri-$C_1$-$C_4$-alkylsilyl group, or a phenoxy, phenyl, phenyl-$C_1$-$C_2$-alkylene, or phenyl-$C_2$-alkenyene group, each optionally substituted on the phenyl or phenoxy group with one or more of halogen atoms, $C_1$-$C_6$ alkyl or $C_1$-$C_6$ alkoxy groups, trihalomethyl groups, phenyl groups or phenoxy groups. p is 0, 1, or 2, Y is a group of the formula —C($R^9R^9$)$_n$—, wherein n is 2, 3, or 4, each $R^9$ independently is hydrogen or $C_1$-$C_4$ alkyl and X is a suitable counter-ion, together with an agriculturally acceptable carrier or diluent.

There is no disclosure or suggestion in any of the above-referenced patents or publications of the insecticidal activity of the compounds of the present invention against members of the order "Homoptera". In addition, there is no disclosure or suggestion in any of the above-referenced patents or publications of the structures of the novel compounds of the present invention.

SUMMARY OF THE INVENTION

The present invention generally relates to insecticidal and acaricidal compositions of substituted benzylamino heterocyclic and heteroaryl derivatives and to certain new and useful compounds, namely certain substituted benzylamino heterocyclic and heteroaryl derivatives that are surprisingly active in the control of insects and acarids when used in the insecticidal and acaricidal compositions and methods of this invention. The insecticidal and acaricidal compositions of the present invention are comprised of at least one of an insecticidally effective amount of a compound of formula I and at least one insecticidally compatible carrier therefor, wherein the compound of formula I is:

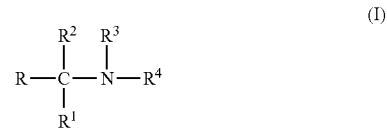

wherein
R, $R^1$, $R^2$ and $R^5$ are described in detail below;
$R^4$ is selected from:

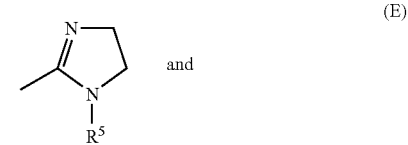

$R^3$ is described in detail below or is taken together with the connecting atom in $R^4$ to form a double bond as in formula (B), formula (D) and formula (F); and
agriculturally acceptable salts thereof.

The present invention also includes compositions containing a pesticidally effective amount of at least one compound of formula I, and optionally, an effective amount of at least one additional compound, with at least one pesticidally compatible carrier.

The present invention also includes methods of controlling insects in an area where control is desired, which comprise applying a pesticidally effective amount of the above composition to the locus of crops, buildings, soil or other areas where insects are present or are expected to be present.

DETAILED DESCRIPTION OF THE INVENTION

The present invention generally relates to insecticidal and acaricidal compositions of substituted benzylamino heterocyclic and heteroaryl derivatives and to certain new and useful compounds, namely certain substituted benzylamino heterocyclic and heteroaryl derivatives that are surprisingly active in the control of insects and acarids when used in the insecticidal and acaricidal compositions and methods of this invention. The insecticidal and acaricidal compositions of the present invention are comprised of at least one of an insecticidally effective amount of a compound of formula I and at least one insecticidally compatible carrier therefor, wherein the compound of formula I is:

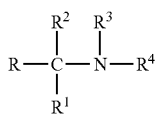
I wherein
R, $R^1$, $R^2$ and $R^5$ are described in detail below;
$R^4$ is selected from:

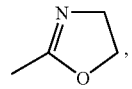 (A)

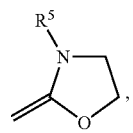 (B)

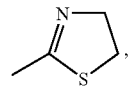 (C)

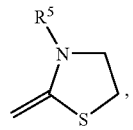 (D)

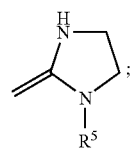 and (E)

(F)

$R^3$ is described in detail below or is taken together with the connecting atom in R to form a double bond as in formula (B), formula (D) and formula (F); and
agriculturally acceptable salts thereof.

More specifically, preferred species of this invention are those insecticidal compositions comprised of compounds of formula IA:

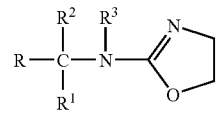
IA wherein
R is selected from 1-naphthyl, phenyl or phenyl substituted with one or two substituents selected from halogen, ($C_1$-$C_2$) alkyl, ($C_1$-$C_2$) alkoxy, ($C_1$-$C_2$) haloalkyl and phenyl;
$R^1$ is selected from hydrogen, ($C_1$-$C_2$) alkyl, ($C_1$-$C_2$) hydroxyalkyl and ($C_1$-$C_2$) haloalkyl;
$R^2$ is selected from hydrogen and ($C_1$-$C_2$) alkyl; and
$R^3$ is selected from hydrogen, ($C_1$-$C_2$) alkyl,

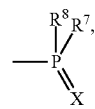 (1)

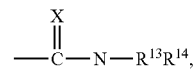 (5)

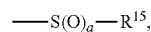 (6)

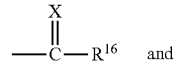 (7)

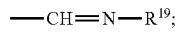 (9)

where
X is oxygen or sulfur;
$R^7$ and $R^8$ are ($C_1$-$C_2$) alkoxy;
$R^{13}$ is ($C_1$-$C_2$) alkyl;
$R^{14}$ is hydrogen;
a is 2;
$R^{15}$ is ($C_1$-$C_2$) dialkylamino;
$R^{16}$ is hydrogen, ($C_1$-$C_2$) alkyl or ($C_1$-$C_2$) alkoxy; and
$R^{19}$ is ($C_1$-$C_2$) alkyl or ($C_1$-$C_2$) alkoxy;
provided that
when R is 1-naphthyl and $R^3$ is hydrogen, then $R^1$ and $R^2$ are other than ($C_1$-$C_2$) alkyl.

More preferred species in this aspect of the invention are those insecticidal compositions comprised of compounds of formula Ia where
R is 2,3-dichlororphenyl or 2,3-dimethylphenyl;
$R^1$ is hydrogen or methyl; and
$R^2$ and $R^3$ are hydrogen.

In another aspect of this invention, preferred species are those insecticidal compositions comprised of formula IB:

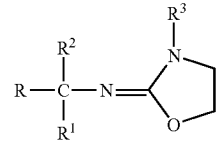
IB wherein
R is 1-naphthyl, phenyl or phenyl substituted with one or two substituents selected from halogen or ($C_1$-$C_2$) alkyl;

$R^1$ is selected from hydrogen, $(C_1-C_4)$ alkyl and $(C_1-C_2)$ haloalkyl;
$R^2$ is hydrogen;
$R^5$ is selected from cyano, $(C_1-C_2)$ alkoxy$(C_1-C_2)$ alkyl, 4-$(C_1-C_2)$ alkoxybenzyl,

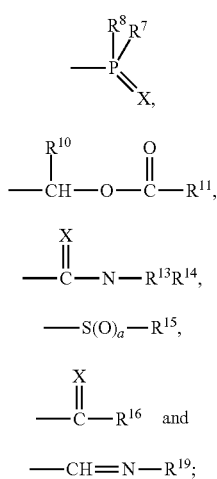

where
X is oxygen or sulfur;
$R^7$ and $R^8$ are $(C_1-C_2)$ alkoxy or $(C_1-C_2)$ haloalkyl;
$R^{10}$ is hydrogen;
$R^{11}$ is $(C_1-C_4)$ alkyl;
$R^{13}$ is $(C_1-C_2)$ alkyl;
$R^{14}$ is hydrogen or $(C_1-C_2)$ alkyl;
a is 2;
$R^{15}$ is $(C_1-C_2)$ alkyl or $(C_1-C_2)$ dialkylamino;
$R^{16}$ is $(C_1-C_2)$ alkyl or $(C_1-C_2)$ alkoxy; and
$R^{19}$ is $(C_1-C_2)$ alkyl or $(C_1-C_2)$ alkoxy;
provided that
when R is 1-naphthyl and $R^5$ is formula (5) where X is sulfur, $R^{13}$ is methyl and $R^{14}$ is hydrogen, then $R^1$ is other than $(C_1-C_2)$ alkyl; and
when R is 3-chloro-2-methylphenyl and $R^1$ is hydrogen, then $R^5$ is other than formula (5) where X is oxygen, $R^{13}$ is methyl and $R^{14}$ is hydrogen or formula (6) where a is 2 and $R^{15}$ is methyl.

More preferred species in this aspect of the invention are those insecticidal compositions comprised of compounds of formula IB where
R is 2,3-dichlorophenyl, 2,3-dimethylphenyl or 3-chloro-2-methylphenyl;
$R^1$ is hydrogen; and
$R^5$ is cyano, formula (1), formula (5) or formula (7).

In another aspect of this invention, preferred species are those insecticidal compositions comprised of formula IC:

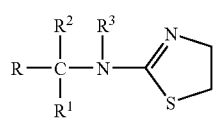

where
R is selected from 1-naphthyl, 2-$(C_1-C_2)$ alkoxyphenyl, 3-$(C_1-C_2)$ alkoxyphenyl, 4-$(C_1-C_2)$ alkoxyphenyl, 2,4-$(C_1-C_2)$ dialkoxyphenyl, phenyl or phenyl substituted with one or two substituents selected from halogen, $(C_1-C_2)$ alkyl and $(C_1-C_2)$ haloalkyl;
$R^1$ is selected from hydrogen, $(C_1-C_3)$ alkyl, phenyl or benzyl;
$R^2$ is hydrogen; and
$R^3$ is selected from hydrogen, $(C_1-C_2)$ alkyl,

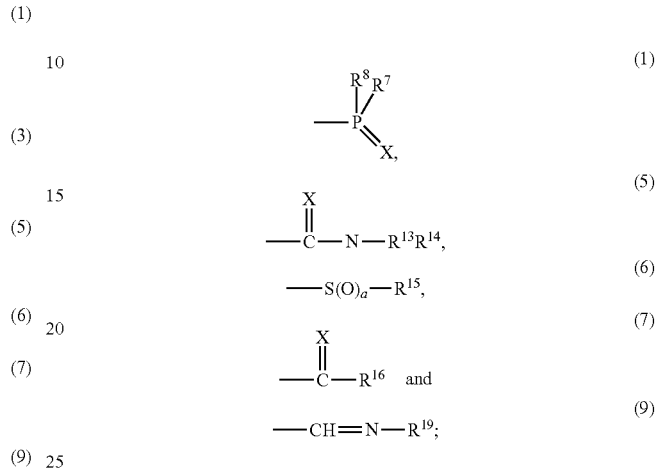

where
X is oxygen or sulfur;
$R^7$ and $R^8$ are $(C_1-C_2)$ alkoxy;
$R^{13}$ is $(C_1-C_2)$ alkyl;
$R^{14}$ is hydrogen;
a is 2;
$R^{15}$ is $(C_1-C_2)$ dialkylamino;
$R^{16}$ is hydrogen, $(C_1-C_2)$ alkyl or $(C_1-C_2)$ alkoxy, and
$R^{19}$ is $(C_1-C_2)$ alkyl or $(C_1-C_2)$ alkoxy;
provided that
when $R^1$ and $R^3$ are hydrogen, then R is other than 2-methylphenyl, 2,4-dimethylphenyl or 2-chloro-6-methylphenyl;
when R is phenyl, $R^1$ and $R^3$ are methyl, then the compound is other than the ((1S)-1-phenylethyl)methyl-1,3-thiazolin-2-ylamine isomer;
when R is phenyl, $R^1$ is methyl and $R^3$ is hydrogen, then the compound is other than the ((1R)-1-phenylethyl)-1,3-thiazolin-2-ylamine isomer; and
when R is 2,3-dichlorophenyl and $R^1$ is hydrogen, then $R^3$ is other than formula (7) where X is oxygen and $R^{16}$ is methoxy.

More preferred species in this aspect of the invention are those insecticidal compositions comprised of compounds of formula Ic where
R is 2,3-dichlororphenyl or 2,3-dimethylphenyl;
$R^1$ is hydrogen or methyl; and
$R^3$ is hydrogen or formula (7) where X is oxygen and $R^{16}$ is $(C_1-C_2)$ alkoxy.

In another aspect of this invention, preferred species are those insecticidal compositions comprised of formula ID:

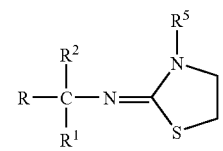

where
R is phenyl optionally substituted with one or two substituents selected from halogen or $(C_1-C_2)$ alkyl;
$R^1$ and $R^2$ are hydrogen; and
$R^5$ is selected from

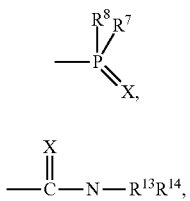
(1)

(5)

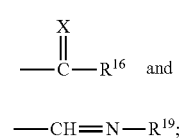

$-S(O)_a-R^{15}$, (6)

(7)

(9)

where
X is oxygen or sulfur;
$R^7$ and $R^8$ are $(C_1-C_2)$ alkoxy;
$R^{13}$ is $(C_1-C_2)$ alkyl;
$R^{14}$ is hydrogen;
a is 2;
$R^{15}$ is $(C_1-C_2)$ dialkylamino;
$R^{16}$ is hydrogen, $(C_1-C_2)$ alkyl or $(C_1-C_2)$ alkoxy; and
$R^{19}$ is $(C_1-C_2)$ alkyl or $(C_1-C_2)$ alkoxy.

More preferred species in this aspect of the invention are those insecticidal compositions comprised of compounds of formula ID where
R is 2,3-dichlorophenyl, 2,3-dimethylphenyl;
$R^5$ is formula (I) where X is sulfur or formula (7) where X is oxygen and $R^{16}$ is $(C_1-C_2)$ alkoxy.

In another aspect of this invention, preferred species are those insecticidal compositions comprised of formula IE:

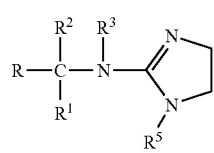
IE where
R is selected from 1-naphthyl, phenyl or phenyl substituted with one or two substituents selected from halogen, $(C_1-C_2)$ alkyl and $(C_1-C_2)$ haloalkyl;
$R^1$ is selected from hydrogen, $(C_1-C_3)$ alkyl, phenyl or benzyl;
$R^2$ is hydrogen; and
$R^3$ is selected from hydrogen, $(C_1-C_2)$ alkyl,

(1)

(5)

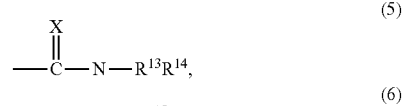

$-S(O)_a-R^{15}$, (6)

(7)

(9)

where
X is oxygen or sulfur;
$R^7$ and $R^8$ are $(C_1-C_2)$ alkoxy-,
$R^{13}$ is $(C_1-C_2)$ alkyl;
$R^{14}$ is hydrogen or $(C_1-C_2)$ alkyl;
a is 2;
$R^{15}$ is $(C_1-C_2)$ alkyl or $(C_1-C_2)$ dialkylamino;
$R^{16}$ is hydrogen, $(C_1-C_2)$ alkyl or $(C_1-C_2)$ alkoxy; and
$R^{19}$ is $(C_1-C_2)$ alkyl or $(C_1-C_2)$ alkoxy.

In another aspect of this invention, preferred species are those insecticidal compositions comprised of formula IF:

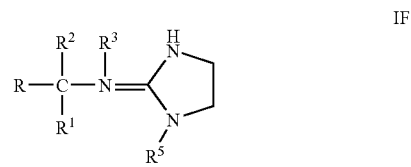
IF where
R is phenyl optionally substituted with one or two substituents selected from halogen or $(C_1-C_2)$ alkyl;
$R^1$ and $R^2$ are hydrogen; and
$R^5$ is selected from cyano,

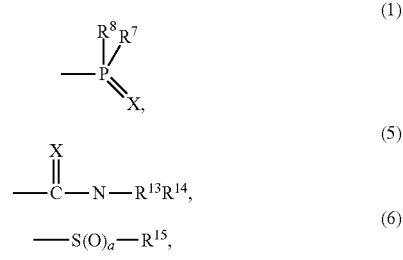
(1)

(5)

(6)

(7)

(9)

where
X is oxygen or sulfur;
$R^7$ and $R^8$ are $(C_1-C_2)$ alkoxy;
$R^{13}$ is $(C_1-C_2)$ alkyl;
$R^{14}$ is hydrogen or $(C_1-C_2)$ alkyl;

a is 2;
R$^{15}$ is (C$_1$-C$_2$) alkyl or (C$_1$-C$_2$) dialkylamino;
R$^{16}$ is hydrogen, (C$_1$-C$_2$) alkyl or (C$_1$-C$_2$) alkoxy, and
R$^{19}$ is (C$_1$-C$_2$) alkyl or (C$_1$-C$_2$) alkoxy.

Certain of the substituted benzylamino heterocyclic and heteroaryl derivatives, useful in the compositions of the present invention, are novel compounds. Many of these compounds are represented by formula IG:

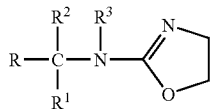
(IG)

wherein
R is selected from 1-naphthyl, phenyl or phenyl substituted with one or two substituents selected from halogen, (C$_1$-C$_2$) alkyl, (C$_1$-C$_2$) alkoxy, (C$_1$-C$_2$) haloalkyl and phenyl;
R$^1$ is selected from hydrogen, (C$_1$-C$_2$) alkyl, (C$_1$-C$_2$) hydroxyalkyl and (C$_1$-C$_2$) haloalkyl;
R$^2$ is selected from hydrogen and (C$_1$-C$_2$) alkyl; and
R$^3$ is selected from hydrogen, (C$_1$-C$_2$) alkyl,

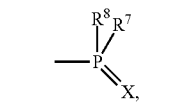
(1)

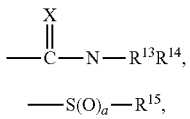
(5)

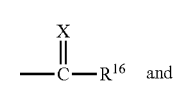
(6)

(7)

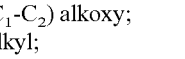
and
(9)

—CH=N—R$^{19}$;

where
X is oxygen or sulfur;
R$^7$ and R$^8$ are (C$_1$-C$_2$) alkoxy;
R$^{13}$ is (C$_1$-C$_2$) alkyl;
R$^{14}$ is hydrogen;
a is 2;
R$^{15}$ is (C$_1$-C$_2$) dialkylamino;
R$^{16}$ is hydrogen, (C$_1$-C$_2$) alkyl or (C$_1$-C$_2$) alkoxy; and
R$^{19}$ is (C$_1$-C$_2$) alkyl or (C$_1$-C$_2$) alkoxy; and agriculturally acceptable salts thereof;
provided that
when R$^1$ is methyl and R$^2$ and R$^3$ are hydrogen, then R is other than phenyl;
when R is 1-naphthyl and R$^3$ is hydrogen, then R$^1$ and R$^2$ are other than (C$_1$-C$_2$) alkyl; and
when R$^1$, R$^2$ and R$^3$ are hydrogen, then R is other than 2-chlorophenyl, 2-fluorophenyl, 2-methylphenyl, 4-chlorophenyl, 3-trifluoromethylphenyl, 3,4-dichlorophenyl and 3,5-dichlorophenyl.

Other substituted benzylamino heterocyclic and heteroaryl derivatives, useful in the compositions of the present invention, are novel compounds. These compounds are represented by formula IH:

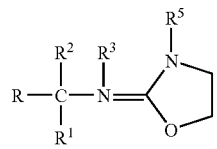
IH wherein
R is 1-naphthyl, phenyl or phenyl substituted with one or two substituents selected from halogen or (C$_1$-C$_2$) alkyl;
R$^1$ is selected from hydrogen, (C$_1$-C$_4$) alkyl and (C$_1$-C$_2$) haloalkyl;
R$^2$ is hydrogen;
R$^5$ is selected from cyano, (C$_1$-C$_2$) alkoxy(C$_1$-C$_2$) alkyl, 4-(C$_1$-C$_2$) alkoxybenzyl, (1)

(3)

(5)

(6)

(7)

and (9)

—CH=N—R$^{19}$;

where
X is oxygen or sulfur;
R$^7$ and R$^8$ are (C$_1$-C$_2$) alkoxy or (C$_1$-C$_2$) haloalkyl;
R$^{10}$ is hydrogen;
R$^{11}$ is (C$_1$-C$_4$) alkyl;
R$^{13}$ is (C$_1$-C$_2$) alkyl;
R$^{14}$ is hydrogen or (C$_1$-C$_2$) alkyl;
a is 2;
R$^{15}$ is (C$_1$-C$_2$) alkyl or (C$_1$-C$_2$) dialkylamino;
R$^{16}$ is (C$_1$-C$_2$) alkyl or (C$_1$-C$_2$) alkoxy;
R$^{19}$ is (C$_1$-C$_2$) alkyl or (C$_1$-C$_2$) alkoxy; and
agriculturally acceptable salts thereof;
provided that
when R is 1-naphthyl and R$^5$ is formula (5) where X is sulfur, R$^{13}$ is methyl and R$^{14}$ is hydrogen, then R$^1$ is other than (C$_1$-C$_4$) alkyl; and
when R is 3-chloro-2-methylphenyl and R$^1$ is hydrogen, then R$^5$ is other than formula (5) where X is oxygen, R$^{13}$ is methyl and R$^{14}$ is hydrogen or formula (6) where R$^{15}$ is methyl.

Still other substituted benzylamino heterocyclic and heteroaryl derivatives, useful in the compositions of the present invention, are novel compounds. These compounds are represented by formula IJ:

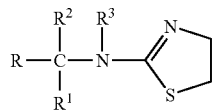

IJ where

R is selected from 1-naphthyl, 2-($C_1$-$C_2$) alkoxyphenyl, 3-($C_1$-$C_2$) alkoxyphenyl, 4-($C_1$-$C_2$) alkoxyphenyl, 2,4-($C_1$-$C_2$) dialkoxyphenyl, phenyl or phenyl substituted with one or two substituents selected from halogen, ($C_1$-$C_2$) alkyl and ($C_1$-$C_2$) haloalkyl;

$R^1$ is selected from hydrogen, ($C_1$-$C_3$) alkyl, phenyl or benzyl;

$R^2$ is hydrogen; and $R^3$ is selected from hydrogen, ($C_1$-$C_2$) alkyl,

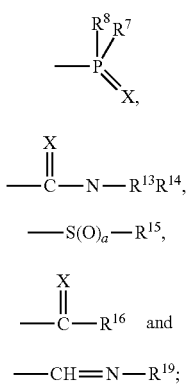

(1)

(5)

(6)

(7)

(9)

where

X is oxygen or sulfur;

$R^7$ and $R^8$ are ($C_1$-$C_2$) alkoxy;

$R^{13}$ is ($C_1$-$C_2$) alkyl;

$R^{14}$ is hydrogen;

a is 2;

$R^{15}$ is ($C_1$-$C_2$) dialkylamino;

$R^{16}$ is hydrogen, ($C_1$-$C_2$) alkyl or ($C_1$-$C_2$) alkoxy, $R^{19}$ is ($C_1$-$C_2$) alkyl or ($C_1$-$C_2$) alkoxy; and agriculturally acceptable salts thereof;

provided that when R is other than 2,3-dimethylphenyl, then at least one of $R^1$ or $R^3$ is other than hydrogen;

when R is phenyl, $R^1$ and $R^3$ are methyl, then the compound is other than the ((1S)-1-phenylethyl)methyl-1,3-thiazolin-2-ylamine isomer;

when R is phenyl, $R^1$ is methyl $R^3$ is hydrogen, then the compound is other than the ((1R)-1-phenylethyl)-1,3-thiazolin-2-ylamine isomer; and when R is 2,3-dichlorophenyl and $R^1$ is hydrogen, then $R^3$ is other than formula (7) where X is oxygen and $R^{16}$ is methoxy.

Other substituted benzylamino heterocyclic and heteroaryl derivatives, useful in the compositions of the present invention, are novel compounds. These compounds are represented by formula IK:

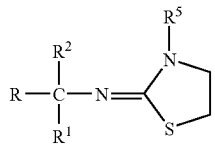

IK where

R is phenyl optionally substituted with one or two substituents selected from halogen or ($C_1$-$C_2$) alkyl;

$R^1$ and $R^2$ are hydrogen; and $R^5$ is selected from (1)

(5)

(6)

(7)

(9)

where

X is oxygen or sulfur;

$R^7$ and $R^8$ are ($C_1$-$C_2$) alkoxy;

$R^{13}$ is ($C_1$-$C_2$) alkyl;

$R^{14}$ is hydrogen;

a is 2;

$R^{15}$ is ($C_1$-$C_2$) dialkylamino;

$R^{16}$ is hydrogen, ($C_1$-$C_2$) alkyl or ($C_1$-$C_2$) alkoxy;

$R^{19}$ is ($C_1$-$C_2$) alkyl or ($C_1$-$C_2$) alkoxy; and agriculturally acceptable salts thereof.

Still other substituted benzylamino heterocyclic and heteroaryl derivatives, useful in the compositions of the present invention, are novel compounds. These compounds are represented by formula IL:

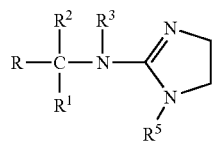

IL where

R is selected from 1-naphthyl, phenyl or phenyl substituted with one or two substituents selected from halogen, ($C_1$-$C_2$) alkyl and ($C_1$-$C_2$) haloalkyl;

$R^1$ is selected from hydrogen, ($C_1$-$C_3$) alkyl, phenyl or benzyl;

$R^2$ is hydrogen; and $R^3$ is selected from hydrogen, ($C_1$-$C_2$) alkyl,

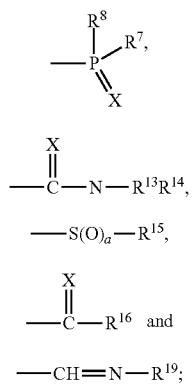

where
R is phenyl optionally substituted with one or two substituents selected from halogen or $(C_1-C_2)$ alkyl;
$R^1$ and $R^2$ are hydrogen; and
$R^5$ is selected from cyano,

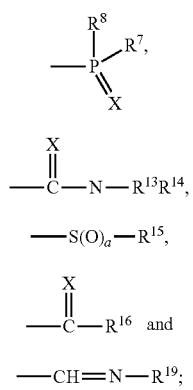

where
X is oxygen or sulfur;
$R^7$ and $R^8$ are $(C_1-C_2)$ alkoxy;
$R^{13}$ is $(C_1-C_2)$ alkyl;
$R^{14}$ is hydrogen or $(C_1-C_2)$ alkyl;
a is 2;
$R^{15}$ is $(C_1-C_2)$ alkyl or $(C_1-C_2)$ dialkylamino;
$R^{16}$ is hydrogen, $(C_1-C_2)$ alkyl or $(C_1-C_2)$ alkoxy; and
$R^{19}$ is $(C_1-C_2)$ alkyl or $(C_1-C_2)$ alkoxy; and
agriculturally acceptable salts thereof.

Other substituted benzylamino heterocyclic and heteroaryl derivatives, useful in the compositions of the present invention, are novel compounds. These compounds are represented by formula IM:

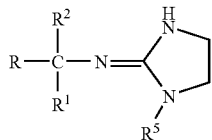

where
R is phenyl optionally substituted with one or two substituents selected from halogen or $(C_1-C_2)$ alkyl;
$R^1$ and $R^2$ are hydrogen; and
$R^5$ is selected from cyano, where
X is oxygen or sulfur;
$R^7$ and $R^8$ are $(C_1-C_2)$ alkoxy,
$R^{13}$ is $(C_1-C_2)$ alkyl;
$R^{14}$ is hydrogen or $(C_1-C_2)$ alkyl;
a is 2;
$R^{15}$ is $(C_1-C_2)$ alkyl or $(C_1-C_2)$ dialkylamino;
$R^{16}$ is hydrogen, $(C_1-C_2)$ alkyl or $(C_1-C_2)$ alkoxy and
$R^{19}$ is $(C_1-C_2)$ alkyl or $(C_1-C_2)$ alkoxy, and
agriculturally acceptable salts thereof.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties.

The compounds of the present invention may exist as tautomers, in which migration of a hydrogen atom within the molecule results in two or more structures, which are in equilibrium. For example, compounds of formula I wherein $R^4$ is selected from (A) and (B), (C) and (D) or (E) and (F) may exist in tautomeric forms as shown in formulae below. Such tautomerism is well known as is described in S. Patai (The Chemistry of Functional Groups: Amidines and Imidates, Vol 2, 1991, pages 259-262). It will be understood that all such tautomeric forms are embraced by the present invention.

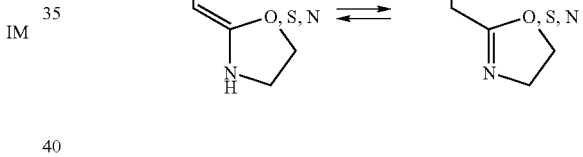

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I with at least one insecticidally compatible carrier therefor.

Another aspect of the present invention relates to compositions containing an insecticidally effective amount of at least one compound of formula I, and an effective amount of at least one additional compound, with at least one insecticidally compatible carrier therefor.

Another aspect of the present invention relates to methods of controlling insects by applying an insecticidally effective amount of a composition set forth above to a locus of crops such as, without limitation, cereals, cotton, vegetables, and fruits, or other areas where insects are present or are expected to be present.

The present invention also includes the use of the compounds and compositions set forth herein for control of non-agricultural insect species, for example, dry wood termites and subterranean termites; as well as for use as pharmaceutical agents and compositions thereof. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent; and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "heterocyclic" refers to a non-aromatic ring structure of four to eight atoms consisting of carbon and nitrogen, and may include oxygen or sulfur. Five member rings include, without limitation, for example, oxazolidine and thiazoline. Six member rings include, without limitation, for example, piperazine, piperidine, morpholine and thiomorpholine. The term "aryl" refers to an aromatic ring structure, including fused rings, having four to ten carbon atoms, for example, phenyl or naphthyl and 5,6,7,8-tetrahydronaphthyl. The term "heteroaryl" refers to an aromatic ring structure, including fused rings, in which at least one of the atoms is other than carbon, for example, without limitation, sulfur, oxygen, or nitrogen. The term "brine" refers to an aqueous saturated sodium chloride solution. The term "TEA" refers to triethylamine. The term "THF" refers to tetrahydrofuran. The term "halogen" or "halo" refers to fluorine, bromine, iodine, or chlorine. The term "ambient temperature", for example, in reference to a chemical reaction mixture temperature refers to a temperature in the range of 20° C. to 30° C. The term "insecticidal" or "acaricidal", "insecticide" or "acaricide" refers to a compound of the present invention, either alone or in admixture with at least one of a second compound, or with at least one compatible carrier, which causes the destruction or the inhibition of action of insects or acarids.

The compounds of the present invention were prepared by methods generally known to those skilled in the art. A number of the compounds of the present invention were prepared in the manner shown in Scheme 1.

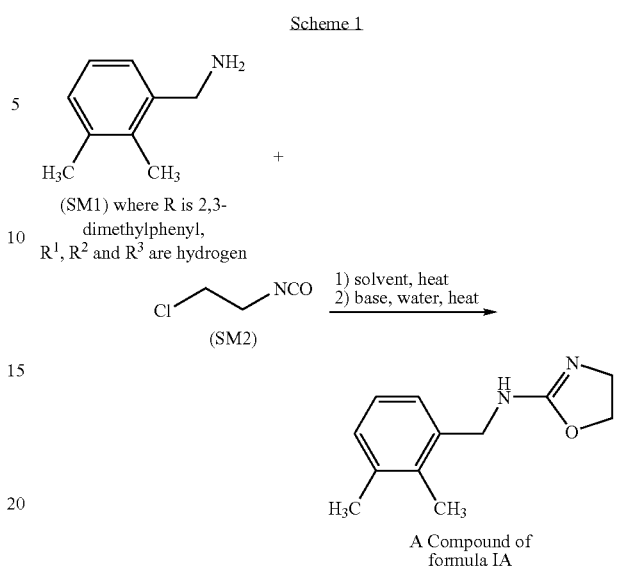

As depicted in Scheme 1, the reaction of an appropriately substituted benzylamine (SM1) and 2-chloroethyl isocyanate (SM2) yielded the appropriately substituted benzyl 1,3-oxazolinyl amine, for example, ((2,3-dimethylphenyl)methyl)-1,3-oxazolin-2-ylamine, a compound of formula IA described in detail in Example 1 set forth below.

Scheme 2 provides a general method for the preparation of compounds of formula I in which the $R^5$ substituent is other than hydrogen.

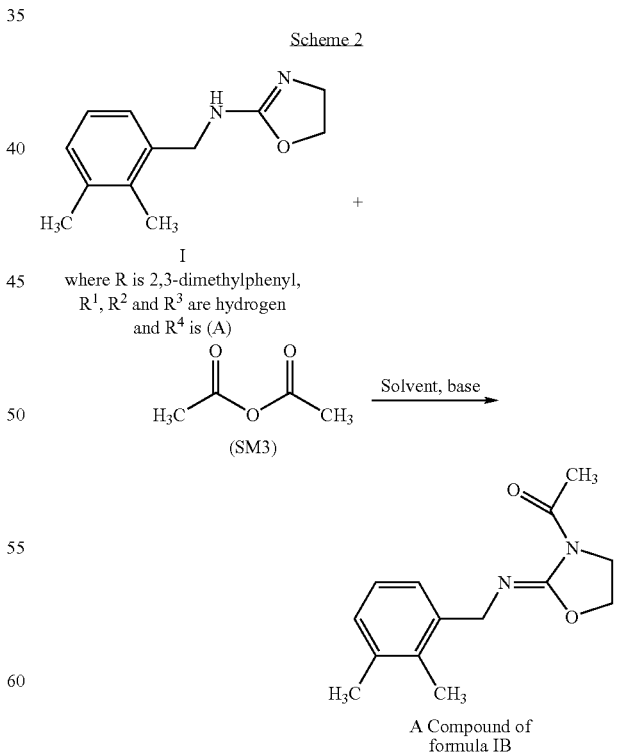

As depicted in Scheme 2, the reaction of an appropriately substituted benzyl 1,3-oxazolinyl amine (a compound of formula IA) with acetic anhydride (SM3) under basic conditions, in an appropriate solvent yielded the corresponding 3-acetyl-2-substituted methylamino-1,3-oxazolidine, for example, 3-acetyl-(1-aza-2-(2,3-dimethylphenyl)ethylidene)-1,3-oxazolidine, a compound of formula IB described in detail in Example 2 set forth below.

Scheme 3 provides method for the preparation of compounds of formula IC.

Scheme 3

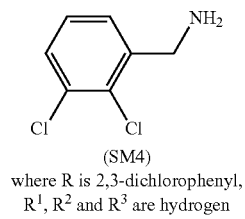
(SM4)
where R is 2,3-dichlorophenyl,
R¹, R² and R³ are hydrogen

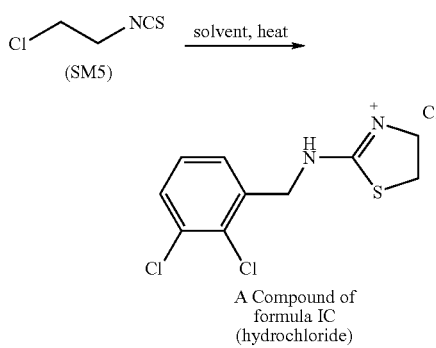

As depicted in Scheme 3, the reaction of a substituted benzylamine (SM4) and 2-chloroethyl isothiocyanate (SM5) yielded the appropriately substituted benzyl 1,3-thiazolinyl amine hydrochloride, for example, ((2,3-dichlorophenyl)methyl)-1,3-thiazolin-2-ylamine hydrochloride, a compound of formula IC described in detail in Example 3, Step A set forth below. Treatment of the hydrochloride of a compound of formula IC with a base in an appropriate solvent produced the corresponding substituted benzyl 1,3-thiazolinyl amine, for example ((2,3-dichlorophenyl)methyl)-1,3-thiazolin-2-ylamine, a compound of formula IC described in detail in Example 3, Step B set forth below.

Scheme 4 provides method for the preparation of compounds of formula IC and formula ID.

Scheme 4

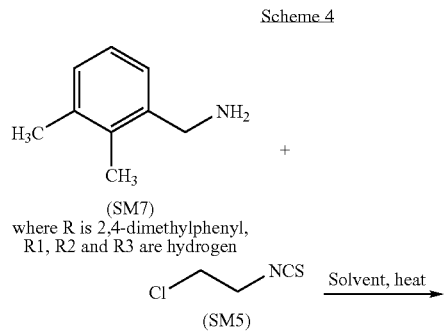
(SM7)
where R is 2,4-dimethylphenyl,
R1, R2 and R3 are hydrogen

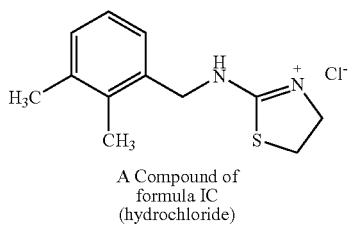

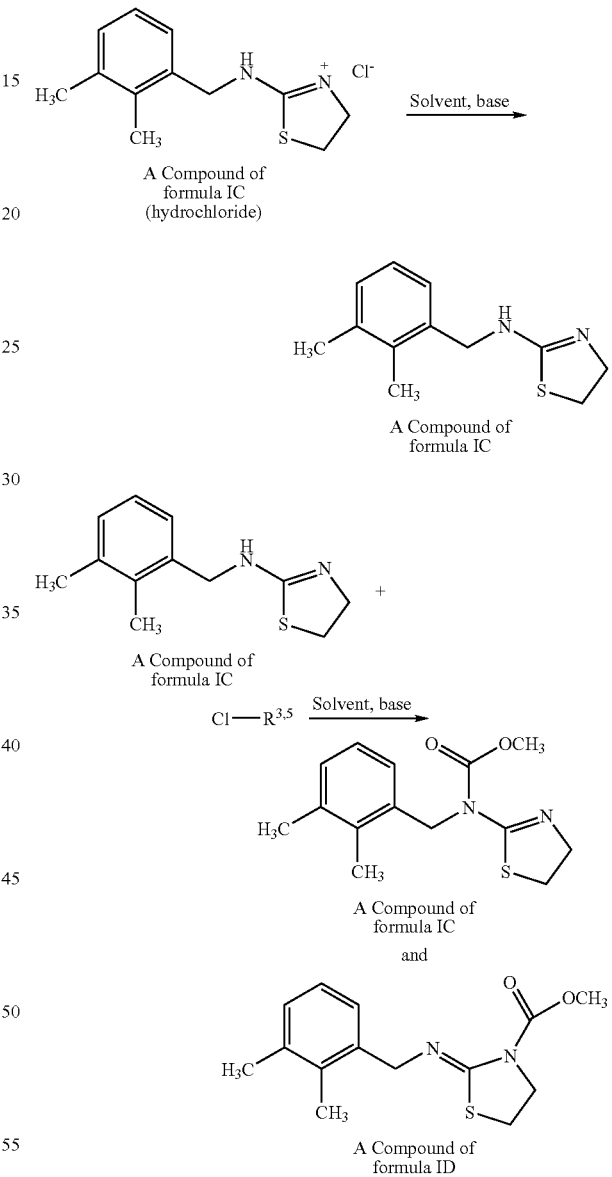

As depicted in Scheme 4, the reaction of a disubstituted benzylamine, for example, 2,3-dimethylbenzylamine, and 2-chloroethyl isothiocyanate (SM5) yielded the appropriately substituted benzyl 1,3-thiazolinyl amine hydrochloride, for example, ((2,3-dimethylphenyl)methyl)-1,3-thiazolin-2-ylamine hydrochloride, a compound of formula IC described in detail in Example 4, Step A set forth below. Treatment of the hydrochloride of a compound of formula IC with a base in an appropriate solvent produced the corresponding substituted benzyl 1,3-thiazolinyl amine, for example ((2,3-dimethylphenyl)methyl)-1,3-thiazolin-2-ylamine, a compound of formula IC described in detail in Example 4, Step B set forth below. The reaction of the substituted benzyl 1,3-thiazolinyl amine with, for example, methyl chloroformate, under basic conditions yielded two compounds. The first, a compound of formula IC where the $R^3$ substituent is other than hydrogen, for example, methyl 2-(1-aza-2-(2,3-dimethylphenyl)ethylidene)-1,3-thiazolidine-3-carboxylate, and the second, a compound of formula ID where the R5 substituent is other than hydrogen, for example, N-((2,3-dimethylphenyl)methyl)methoxy-N-(1,3-thiazolin-2-yl)carboxamide, both described in detail in Example 4, Step C set forth below.

Scheme 5 provides a general method for the preparation of compounds of formula I where the $R^1$ substituent is other than hydrogen.

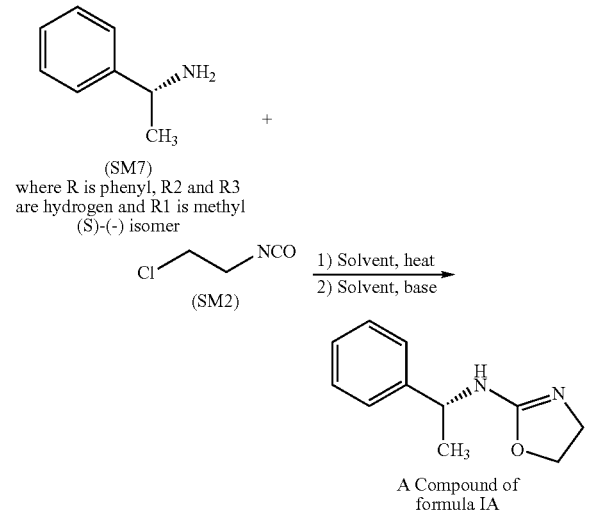

As depicted in Scheme 5, the reaction of an appropriately substituted isomer of a phenylethylamine (SM7), for example, (S)-(−)-phenylethylamine, and 2-chloroethyl isocyanate (SM2) yielded the appropriately substituted phenylethyl 1,3-oxazolinyl amine, for example, ((S)-1-phenyl-ethyl)-1,3-oxazolin-2-ylamine, a compound of formula IA described in detail in Example 5 set forth below.

One skilled in the art will, of course, recognize that the formulation and mode of application of a toxicant may affect the activity of the material in a given application. Thus, for agricultural use the present insecticidal compounds may be formulated as granules of relatively large particle size (for example, ⁵⁄₁₆ or ⅜ US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal and acaricidal compounds of this invention may be formulated and/or applied with at least one additional compound. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Additional compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with at least one additional compound, e.g., with other pesticides such as herbicides, the herbicides include, without limitation, for example: N-(phosphonomethyl)glycine such as glyphosate; aryloxyalkanoic acids such as 2,4D, MCPA, and MCPP; ureas such as isoproturon; imidazolinones such as imazapyr, imazethapyr, and imazaquin; diphenyl ethers such as acifluorfen, bifenox, and fomasafen; hydroxybenzonitriles such as ioxynil and bromoxynil; sulfonylureas such as chlorimuron, achlorsulfuron, bensulfuron, pyrazosulfuron, thifensulfuron, and triasulfuron; 2-(4-aryloxyphenoxy)alkanoic acids such as fenoxaprop, fluazifop, quizalofop, and diclofop; benzothiadiazinones such as bentazone; 2-chloroacetanilides such as butachlor, metolachlor, acetochlor, and dimethenamide; arenecarboxylic acids such as dicamba; pyridyloxyacetic acids such as fluoroxypyr; aryl triazolinones such as sulfentrazone and carfentrazone-ethyl; isoxazolidinones such as clomazone; and other herbicides.

When the active insecticidal compounds of the present invention are used in combination with at least one additional compound, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, beta-cypermethrin, zeta-cypermethrin bifenthrin, cypermethrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with at least one additional compound, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with at least one additional compound, e.g., with other pesticides such as nematicides, the nematicides include, for example: carbofuran, carbosulfan, terbufos, aldecarb, ethoprop, fenamphos, oxamyl, isazofos, cadusafos, and other nematicides.

When the active insecticidal compounds of the present invention are used in combination with at least one additional compound, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with at least one additional compound, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria.*

Fertilizers are plant food supplements, which commonly contain nitrogen, phosphorus, and potassium. When the active insecticidal compounds of the present invention are used in combination with at least one additional compound, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

The compounds of formula I can be synthesized by methods that are individually known to one skilled in the art from intermediate compounds readily available in commerce.

Example 1

This example illustrates one protocol for the preparation of ((2,3-dimethylphenyl)methyl)-1,3-oxazolin-2-ylamine (Compound A25)

A mixture of 1.0 gram (0.0074 mole) of 2,3-dimethylbenzylamine and 0.69 gram (0.0081 mole) of 2-chloroethylisocyanate in 10 mL of 1,4-dioxane was heated to reflux where it stirred for about 18 hours. The reaction mixture was allowed to cool and an aqueous solution of sodium hydroxide (4.0 mL of a 3.0 molar solution) was added. The reaction mixture was heated to reflux for about 18 hours then allowed to cool to ambient temperature. The reaction mixture was concentrated under reduced pressure to leave a viscous oil residue. The residue was suspended in 50 mL of ethyl acetate and washed with 20 mL of water. The organic phase was extracted with 20 mL of 3.0 molar aqueous hydrochloric acid. The aqueous extract was made basic by adding 3.0 molar aqueous sodium hydroxide and the basic mixture was extracted with 50 mL of ethyl acetate. The extract was dried with sodium sulfate, filtered and the filtrate concentrated under reduced pressure to yield 0.81 gram of the title compound as an oil. The NMR spectrum was consistent with the proposed structure.

Example 2

This example illustrates one protocol for the preparation of 3-acetyl-(1-aza-2-(2,3-dimethylphenyl)ethylidene)-1,3-oxazolidine (Compound B2)

Acetic anhydride (1.0 gram, 0.002 mole) was added to a stirred, cold (5° C.) mixture of 0.2 gram (0.002 mole) of ((2,3-dimethylphenyl)methyl)-1,3-oxazolin-2-ylamine (Compound A25), 0.1 gram (0.0008 mole) of magnesium sulfate and 0.4 gram (0.006 mole) of potassium carbonate in 10 mL of diethyl ether. The reaction mixture was allowed to warm to ambient temperature where it stirred for two hours. The reaction mixture was filtered, the filter cake was rinsed with diethyl ether, and the combined filtrates were concentrated under reduced pressure to leave a residue. The residue was stirred with a mixture of 1 mL of diethyl ether and 4 mL of hexanes. A precipitate formed and was collected by filtration, rinsed with hexanes and dried under reduced pressure to yield 0.16 gram of the title compound. The NMR spectrum was consistent with the proposed structure.

Example 3

This example illustrates one protocol for the preparation of ((2,3-dichlorophenyl)methyl)-1,3-thiazolin-2-ylamine hydrochloride (Compound C7) and ((2,3-dichlorophenyl)methyl)-1,3-thiazolin-2-ylamine (Compound C9)

Step A Synthesis of ((2,3-dichlorophenyl)methyl)-1,3-thiazolin-2-ylamine hydrochloride (Compound C7)

A mixture of 0.5 gram (0.0028 mole) of 2,3-dichlorobenzylamine and 0.27 gram (0.0081 mole) of 2-chloroethylisothiocyanate in 10 mL of 1,4-dioxane was placed in a sealed reaction vial. The reaction mixture was heated to 80° C. where it stirred for about 18 hours. The reaction mixture was allowed to cool and a solid precipitate that had formed was collected by filtration. The solid was rinsed with diethyl ether and was dried under reduced pressure to yield 0.68 gram of the title compound. The NMR spectrum was consistent with the proposed structure.

Step B Synthesis of ((2,3-dichlorophenyl)methyl)-1,3-thiazolin-2-ylamine (Compound C9)

A mixture of 0.36 gram (0.0012 mole) of ((2,3-dichlorophenyl)methyl)-1,3-thiazolin-2-ylamine hydrochloride (Compound C7) in one mL of water was added to a stirred, cold (ice water bath) mixture of 0.05 gram (0.0013 mole) of sodium hydroxide in 10 mL of water and 10 mL of diethyl ether. The reaction mixture was stirred for 10 minutes, poured into a separatory funnel and was extracted with two 50 mL portions of diethyl ether. The extracts were combined, dried with sodium sulfite and filtered. The filtrate was concentrated under reduced pressure to yield 0.31 gram of the title compound as a white solid. The NMR spectrum was consistent with the proposed structure.

Example 4

This example illustrates one protocol for the preparation of ((2,3-dimethylphenyl)methyl)-1,3-thiazolin-2-ylamine hydrochloride (Compound C11), ((2,3-dimethylphenyl)methyl)-1,3-thiazolin-2-ylamine (Compound C66), methyl 2-(1-aza-2-(2,3-dimethylphenyl)ethylidene)-1,3-thiazolidine-3-carboxylate (Compound C53) and N-((2,3-dimethylphenyl)methyl)methoxy-N-(1,3-thiazolin-2-yl)carboxamide (Compound D5)

Step A Synthesis of ((2,3-dimethylphenyl)methyl)-1,3-thiazolin-2-ylamine hydrochloride (Compound C11)

Under a dry nitrogen atmosphere, a stirred mixture of 5.56 grams (0.041 mole) of 2,3-dimethylbenzylamine and 5.0 grams (0.041 mole) of 2-chloroethylisothiocyanate in 100 mL of 1,4-dioxane was heated to 80° C. where it stirred for about 18 hours. The reaction mixture was allowed to cool and a solid precipitate that had formed was collected by filtration. The solid was rinsed with diethyl ether and was dried under reduced pressure to yield 8.0 grams of the title compound. The NMR spectrum was consistent with the proposed structure.

Step B Synthesis of ((2,3-dimethylphenyl)methyl)-1,3-thiazolin-2-ylamine (Compound C66)

A mixture of 1.4 grams (0.034 mole) of sodium hydroxide in 100 mL of water was added to a stirred, cold (ice water bath) mixture of 8.0 grams (0.031 mole) of ((2,3-dimethylphenyl)methyl)-1,3-thiazolin-2-ylamine hydrochloride (Compound C11) in 100 mL of diethyl ether. The reaction mixture was allowed to warm to ambient temperature where it stirred for two hours. The reaction mixture was poured into a separatory funnel and the organic phase was removed and saved. The aqueous phase was extracted with 100 mL of diethyl ether. The organic extract was combined with the saved organic phase, dried with sodium sulfite and filtered. The filtrate was concentrated under reduced pressure to yield 6.8 grams of the title compound as a white solid, melting point 110-114° C. The NMR spectrum was consistent with the proposed structure.

Step C Synthesis of methyl 2-(1-aza-2-(2,3-dimethylphenyl)ethylidene)-1,3-thiazolidine-3-carboxylate (Compound C53) and N-((2,3-dimethylphenyl)methyl)methoxy-N-(1,3-thiazolin-2-yl)carboxamide (Compound D5)

Under a dry nitrogen atmosphere, a solution of 0.25 gram (0.0011 mole) of ((2,3-dimethylphenyl)methyl)-1,3-thiazolin-2-ylamine dissolved in 10 mL of THF was added to a stirred suspension of 0.08 gram (0.0012 mole) of sodium hydride (60% suspension in oil). The mixture was stirred for 30 minutes, at which time a solution of 0.11 mL (0.0014 mole) of methyl chloroformate in 5 mL of THF was added slowly. The reaction mixture stirred at ambient temperature for about 18 hours. The reaction mixture was heated to 60° C. where it stirred for one hour. The reaction mixture was diluted with 25 mL of brine, then extracted with two 25 mL portions of ethyl acetate. The extracts were combined, washed with 25 mL of water, dried with sodium sulfate and filtered. The filtrate was concentrated under reduced pressure to leave a solid residue. Analysis of the residue by TLC indicated that two compounds were present. The residue was purified by column chromatography on silica gel, eluting with hexanes: methylene chloride (1:1). The appropriate fractions were combined and concentrated under reduced pressure to yield 0.05 gram of methyl 2-(1-aza-2-(2,3-dimethylphenyl)ethylidene)-1,3-thiazolidine-3-carboxylate (Compound C53) and 0.14 gram of N-((2,3-dimethylphenyl)methyl)methoxy-N-(1,3-thiazolin-2-yl)carboxamide (Compound D5). The NMR spectra were consistent with the proposed structures.

Example 5

This example illustrates one protocol for the preparation of ((1S)-1-phenylethyl)-1,3-oxazolin-2-ylamine (Compound A58)

A mixture of 0.5 gram (0.0041 mole) of (S)-(−)-phenylethylamine and 0.44 gram (0.0042 mole) of 2-chloroethylisocyanate in 10 mL of 1,4-dioxane was heated to reflux where it stirred for about 18 hours. The reaction mixture was allowed to cool and an aqueous solution of sodium hydroxide (1.0 mL of a 3.0 molar solution) was added. The reaction mixture was heated to reflux for three hours then allowed to cool to ambient temperature. The reaction mixture was concentrated under reduced pressure to leave a viscous oil residue. The residue was suspended in 50 mL of ethyl acetate and extracted with 10 mL of 3.0 molar aqueous hydrochloric acid. The aqueous extract was made basic by the addition of 3.0 molar aqueous sodium hydroxide. The basic mixture was extracted with two 30 mL portions of ethyl acetate. The extracts were combined, dried with sodium sulfate, filtered and the filtrate concentrated under reduced pressure to yield 0.45 gram of the title compound as a solid. The NMR spectrum was consistent with the proposed structure.

The following table sets forth some additional examples of compounds of formula I useful in the present invention:

TABLE 1

Insecticidal Substituted Benzylamino Heterocyclic Derivatives

I

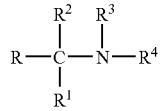

Formula I where $R^4$ is formula (A):

IA

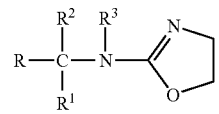

| Cmpd No | R | $R^1$ | $R^2$ | $R^3$ |
|---|---|---|---|---|
| A1 | 2,3-dichloro-phenyl (Cl, Cl) | H | H | H |
| A2 | 2-chloro-phenyl (Cl) | H | H | H |
| A3 | 3-chloro-phenyl (Cl) | H | H | H |

TABLE 1-continued

| | | | | |
|---|---|---|---|---|
| A4 | 4-Cl-C₆H₄- | H | H | H |
| A5 | 2,4-Cl₂-C₆H₃- | H | H | H |
| A6 | 2,5-Cl₂-C₆H₃- | H | H | H |
| A7 | 3,4-Cl₂-C₆H₃- | H | H | H |
| A8 | 3,5-Cl₂-C₆H₃- | H | H | H |
| A9 | 2-CF₃-C₆H₄- | H | H | H |
| A10 | 3-CF₃-C₆H₄- | H | H | H |
| A11 | 4-CF₃-C₆H₄- | H | H | H |
| A12 | 3-OMe-C₆H₄- | H | H | H |
| A13 | 2,3-(OMe)₂-C₆H₃- | H | H | H |
| A14 | 2,4-(OMe)₂-C₆H₃- | H | H | H |
| A15 | 2,5-(OMe)₂-C₆H₃- | H | H | H |

TABLE 1-continued

| | | | | |
|---|---|---|---|---|
| A16 | 2,6-dimethoxyphenyl-methyl (OMe, OMe) | H | H | H |
| A17 | 3,5-dimethoxyphenyl-methyl (MeO, OMe) | H | H | H |
| A18 | 2-methoxyphenyl-methyl (OMe) | H | H | H |
| A19 | 4-methoxyphenyl-methyl (MeO) | H | H | H |
| A20 | 3,4-dimethoxyphenyl-methyl (OMe, MeO) | H | H | H |
| A21 | 3-methylphenyl-methyl (CH₃) | H | H | H |
| A22 | 2,4-dimethylphenyl-methyl (H₃C, CH₃) | H | H | H |
| A23 | 2,5-dimethylphenyl-methyl (H₃C, CH₃) | H | H | H |
| A24 | 4-methylphenyl-methyl (H₃C) | H | H | H |
| A25 | 2,3-dimethylphenyl-methyl (CH₃, CH₃) | H | H | H |
| A26 | 2,5-dimethylphenyl-methyl (H₃C, CH₃) | H | H | H |

TABLE 1-continued

| | | | | |
|---|---|---|---|---|
| A27 | 3,5-dimethylphenyl | H | H | H |
| A28 | phenyl | H | H | H |
| A29 | 2-methylphenyl | H | H | H |
| A30 | 2-chloro-6-methylphenyl | H | H | H |
| A31 | 2-chloro-3-methylphenyl | H | H | H |
| A32 | 2,3-dimethylphenyl | H | H | —COCH$_3$ |
| A33 | 2,3-dimethylphenyl | H | H | —SO$_2$N(CH$_3$)$_2$ |
| A34 | 2,3-dimethylphenyl | H | H | —PO(OC$_2$H$_5$)$_2$ |
| A35 | 2,3-dimethylphenyl | H | H | —PS(OC$_2$H$_5$)$_2$ |
| A36 | 2,3-dimethylphenyl | H | H | —CO$_2$CH$_3$ |

TABLE 1-continued

| | | | | |
|---|---|---|---|---|
| A37 | 2,3-dimethylphenyl | H | H | —CHO |
| A38 | 2,3-dimethylphenyl | H | H | —CONHCH$_3$ |
| A39 | 2,3-dimethylphenyl | H | H | —CSNHCH$_3$ |
| A40 | 2,3-dimethylphenyl | H | H | —CH=NC$_2$H$_5$ |
| A41 | 2,3-dimethylphenyl | H | H | —CH=NOC$_2$H$_5$ |
| A42 | 2,3-dichlorophenyl | H | H | —COCH$_3$ |
| A43 | 2,3-dichlorophenyl | H | H | —SO$_2$N(CH$_3$)$_2$ |
| A44 | 2,3-dichlorophenyl | H | H | —PO(OC$_2$H$_5$)$_2$ |
| A45 | 2,3-dichlorophenyl | H | H | —PS(OC$_2$H$_5$)$_2$ |
| A46 | 2,3-dichlorophenyl | H | H | —CO$_2$CH$_3$ |

TABLE 1-continued

| | | | | |
|---|---|---|---|---|
| A47 | 2,3-dichlorophenyl | H | H | —CHO |
| A48 | 2,3-dichlorophenyl | H | H | —CONHCH₃ |
| A49 | 2,3-dichlorophenyl | H | H | —CSNHCH₃ |
| A50 | 2,3-dichlorophenyl | H | H | —CH=NC₂H₅ |
| A51 | 2,3-dichlorophenyl | H | H | —CH=NOC₂H₅ |
| A52 | phenyl | —CH₃ | H | H |
| A53 | phenyl | —CH₃ | —CH₃ | H |
| A54 | 4-chloro-2-methylphenyl | H | H | H |
| A55 | 4-chloro-2-methylphenyl | H | H | H |
| A56 | 3-chlorophenyl | H | H | —CH₃ |
| A57 | phenyl | H | H | —CH₃ |
| A58* | phenyl | —CH₃ | H | H |

TABLE 1-continued

| | | | | |
|---|---|---|---|---|
| A59** | phenyl | —CH₃ | H | —CH₃ |
| A60* | phenyl | —CH₃ | H | —CH₃ |
| A61** | phenyl | —CH₃ | H | H |
| A62 | 2,3-dichlorophenyl | —CH₃ | H | H |
| A63 | phenyl | —C₂H₅ | H | H |
| A64 | phenyl | phenyl | H | H |
| A65 | 3-chloro-2-fluorophenyl | H | H | H |
| A66 | phenyl | benzyl (—CH₂—C₆H₅) | H | H |
| A67 | 2-methyl-3-chlorophenyl | H | H | H |
| A68 | 4-methyl-3-chlorophenyl | H | H | H |
| A69 | 2,3-dimethylphenyl | —CH₃ | H | H |
| A70 | 2-ethylphenyl | H | H | H |

TABLE 1-continued
| Cmpd No | (structure) | | | |
|---|---|---|---|---|
| A71 | 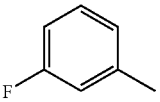 3-fluorophenyl | H | H | H |
| A72 | 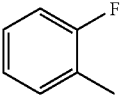 2-fluorophenyl | —CH₃ | H | H |
| A73 | 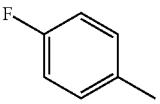 4-fluorophenyl | —CH₃ | H | H |
| A74 | 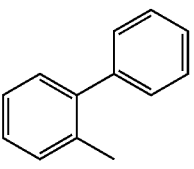 2-biphenyl | H | H | H |
| A75 | 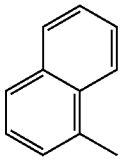 1-naphthyl | H | H | H |
| A76 | 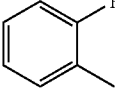 2-fluorophenyl | H | H | H |
| A77 | 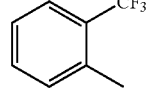 2-(trifluoromethyl)phenyl | —CH₃ | H | H |
\*((1S)-1-phenylethyl) isomer
\*\*((1R)-1-phenylethyl) isomer
Formula I where $R^2$ is hydrogen and $R^4$ is formula (B):
IB
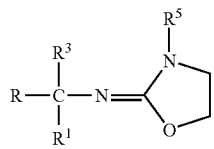
| Cmpd No | R | $R^1$ | $R^5$ |
|---|---|---|---|
| B1 | 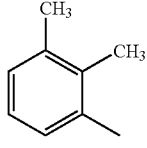 2,3-dimethylphenyl | H | —PS(OC₂H₅)₂ |
| B2 | 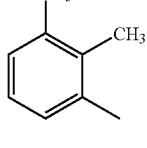 2,3-dimethylphenyl | H | —COCH₃ |

TABLE 1-continued
| | | | |
|---|---|---|---|
| B3 | 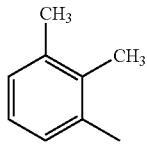 | H | —SO$_2$CH$_3$ |
| B4 | 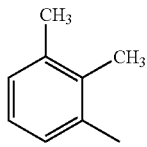 | H | —PS(OCH$_3$)$_2$ |
| B5 | 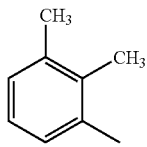 | H | —CH$_2$OCOC(CH$_3$)$_3$ |
| BB6 | 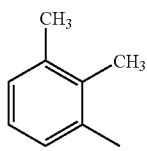 | H | —CON(CH$_3$)$_2$ |
| B7 | 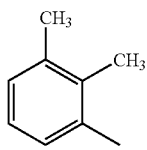 | H | —COC$_2$H$_5$ |
| B8 | 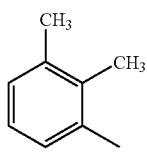 | H | —SO$_2$N(CH$_3$)$_2$ |
| B9 | 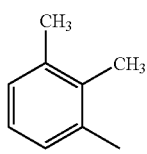 | H | —CONH(CH$_3$) |
| B10 | 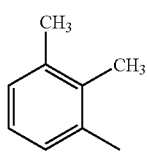 | H | —PO(OC$_2$H$_5$)$_2$ |
| B11 | 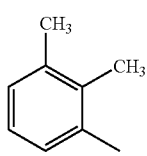 | H | —CO$_2$C$_2$H$_5$ |
| B12 | 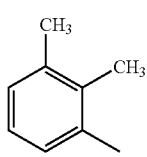 | H | —CO$_2$CH$_3$ |

TABLE 1-continued

| | | | |
|---|---|---|---|
| B13 | 2,3-dimethylphenyl | H | —PO(OCH$_3$)$_2$ |
| B14 | 2,3-dimethylphenyl | H | —PO(N(CH$_3$)$_2$)$_2$ |
| B15 | 2,3-dimethylphenyl | H | —PS(OC$_2$H$_5$)$_2$ |
| B16 | 2,3-dimethylphenyl | H | —CH$_2$OC$_2$H$_5$ |
| B17 | 2,3-dimethylphenyl | H | —CHO |
| B18 | 2,3-dimethylphenyl | H | —CSNHCH$_3$ |
| B19 | 2,3-dimethylphenyl | H | —CH=NC$_2$H$_5$ |
| B20 | 2,3-dimethylphenyl | H | —CH=NOC$_2$H$_5$ |
| B21 | 2,3-dichlorophenyl | H | —COCH$_3$ |
| B22 | 2,3-dichlorophenyl | H | —SO$_2$N(CH$_3$)$_2$ |

TABLE 1-continued

| | | | |
|---|---|---|---|
| B23 | 2,3-dichlorophenyl | H | —PO(OC$_2$H$_5$)$_2$ |
| B24 | 2,3-dichlorophenyl | H | —PS(OC$_2$H$_5$)$_2$ |
| B25 | 2,3-dichlorophenyl | H | —CO$_2$CH$_3$ |
| B26 | 2,3-dichlorophenyl | H | —CHO |
| B27 | 2,3-dichlorophenyl | H | —CONHCH$_3$ |
| B28 | 2,3-dichlorophenyl | H | —CSNHCH$_3$ |
| B29 | 2,3-dichlorophenyl | H | —CH=NC$_2$H$_5$ |
| B30 | 2,3-dichlorophenyl | H | —CH=NOC$_2$H$_5$ |
| B31 | 2,3-dimethylphenyl | H | —CN |
| B32 | 2,3-dimethylphenyl | H | 4-methoxyphenylethyl |

TABLE 1-continued
| | | | |
|---|---|---|---|
| B33 | 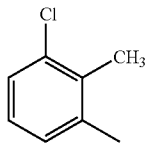 | H | —PS(OC$_2$H$_5$)$_2$ |
| B34 | 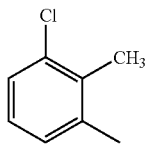 | H | —PO[N(CH$_3$)$_2$]$_2$ |
| B35 | 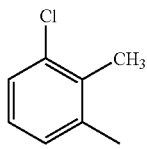 | H | —PS(OCH$_3$)$_2$ |
| B36 | 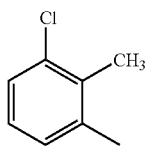 | H | —CN |
| B37 | 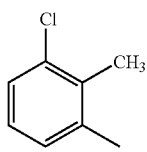 | H | —CSNHCH$_3$ |
| B38 | 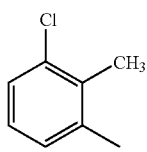 | H | —COCH$_3$ |
| B39 | 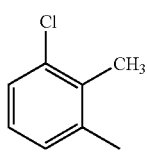 | H | —COC$_2$H$_5$ |
| B40 | 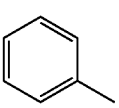 | —C(CH$_3$)$_3$ | —CSNHCH$_3$ |
| B41 | 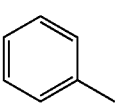 | —CH(CH$_3$)$_2$ | —CSNHCH$_3$ |
| B42 | 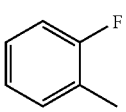 | —CH$_3$ | —CSNHCH$_3$ |
| B43 | 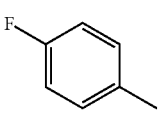 | —CH$_3$ | —CSNHCH$_3$ |

TABLE 1-continued
| Cmpd No | | R | R³ |
|---|---|---|---|
| B44 | 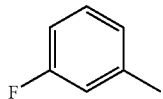 | —CH₃ | —CSNHCH₃ |
| B45 | 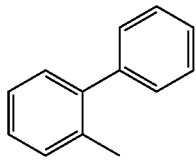 | H | —CSNHCH₃ |
| B46* | 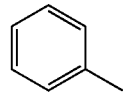 | —CH₃ | —CSNHCH₃ |
| B47 | 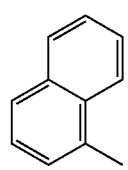 | H | —CSNHCH₃ |
| B48 | 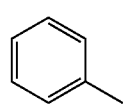 | —CF₃ | —CSNHCH₃ |
| B49* | 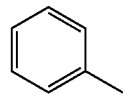 | —CH₃ | —CSNHC₂H₅ |
*(2-((2R)-1-aza-2-phenylpropylidine)(1,3-oxazolidin-3-yl) isomer
Formula I where R² is hydrogen and R⁴ is formula (C):
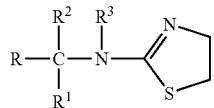
IC
| Cmpd No | R | R¹ | R³ |
|---|---|---|---|
| C1 | 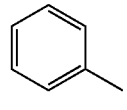 | H | —CH₃ |
| C2 | 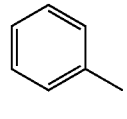 | H | H |
| C3<br>Hydroiodide salt | 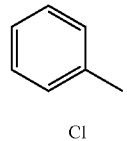 | H | H |
| C4<br>Hydrochloride salt | 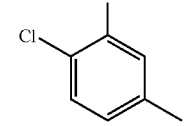 | H | H |
| C5<br>Hydrochloride salt | 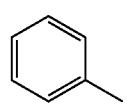 | H | H |

TABLE 1-continued
| | | | |
|---|---|---|---|
| C6 Hydrochloride salt | 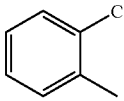 | H | H |
| C7 Hydrochloride salt | 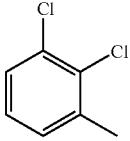 | H | H |
| C8 | 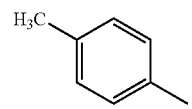 | H | H |
| C9 | 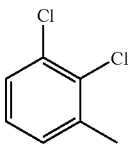 | H | H |
| C10 Hydrochloride salt | 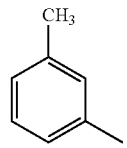 | H | H |
| C11 Hydrochloride salt | 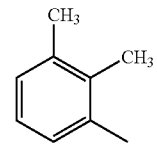 | H | H |
| C12 Hydrochloride salt | 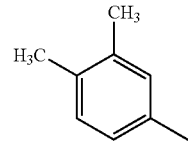 | H | H |
| C13 Hydrochloride salt | 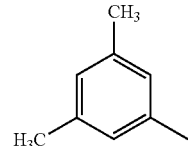 | H | H |
| C14 | 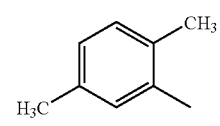 | H | H |
| C15 Hydrochloride salt | 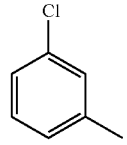 | H | H |
| C16 Hydrochloride salt | 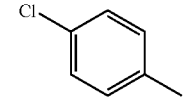 | H | H |

TABLE 1-continued
| | | | |
|---|---|---|---|
| C17 Hydrochloride salt | 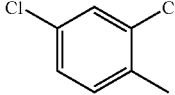 | H | H |
| C18 Hydrochloride salt | 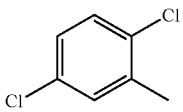 | H | H |
| C19 Hydrochloride salt | 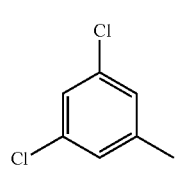 | H | H |
| C20 Hydrochloride salt | 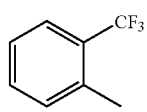 | H | H |
| C21 Hydrochloride salt | 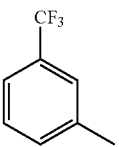 | H | H |
| C22 Hydrochloride salt | 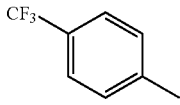 | H | H |
| C23 Hydrochloride salt | 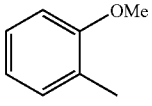 | H | H |
| C24 Hydrochloride salt | 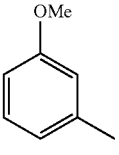 | H | H |
| C25 | 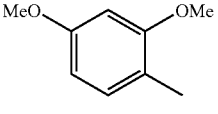 | H | H |
| C26 | 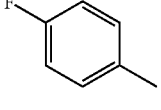 | H | H |
| C27 | 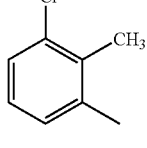 | H | H |
| C28 | 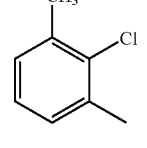 | H | H |

TABLE 1-continued

| | | | |
|---|---|---|---|
| C29 | 2,3-dimethylphenyl | H | —COCH$_3$ |
| C30 | 2,3-dimethylphenyl | H | —SO$_2$N(CH$_3$)$_2$ |
| C31 | 2,3-dimethylphenyl | H | —PO(OC$_2$H$_5$)$_2$ |
| C32 | 2,3-dimethylphenyl | H | —PS(OC$_2$H$_5$)$_2$ |
| C33 | 2,3-dimethylphenyl | H | —CO$_2$CH$_3$ |
| C34 | 2,3-dimethylphenyl | H | —CHO |
| C35 | 2,3-dimethylphenyl | H | —CONHCH$_3$ |
| C36 | 2,3-dimethylphenyl | H | —CSNHCH$_3$ |
| C37 | 2,3-dimethylphenyl | H | —CH=NC$_2$H$_5$ |
| C38 | 2,3-dimethylphenyl | H | —CH=NOC$_2$H$_5$ |

TABLE 1-continued

| | | | |
|---|---|---|---|
| C39 | 2,3-dichlorophenyl | H | —COCH$_3$ |
| C40 | 2,3-dichlorophenyl | H | —SO$_2$N(CH$_3$)$_2$ |
| C41 | 2,3-dichlorophenyl | H | —PO(OC$_2$H$_5$)$_2$ |
| C42 | 2,3-dichlorophenyl | H | —PS(OC$_2$H$_5$)$_2$ |
| C43 | 2,3-dichlorophenyl | H | —CO$_2$CH$_3$ |
| C44 | 2,3-dichlorophenyl | H | —CHO |
| C45 | 2,3-dichlorophenyl | H | —CONHCH$_3$ |
| C46 | 2,3-dichlorophenyl | H | —CSNHCH$_3$ |
| C47 | 2,3-dichlorophenyl | H | —CH=NC$_2$H$_5$ |
| C48 | 2,3-dichlorophenyl | H | —CH=NOC$_2$H$_5$ |

TABLE 1-continued
| | | | |
|---|---|---|---|
| C49 | 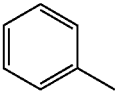 | —CH₃ | H |
| C50 | 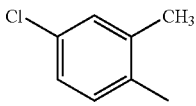 | H | H |
| C51 | 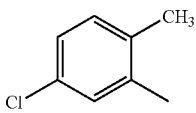 | H | H |
| C52 | 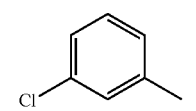 | H | —CH₃ |
| C53 | 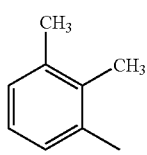 | H | —CO₂CH₃ |
| C54* | 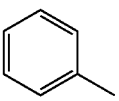 | —CH₃ | H |
| C55** | 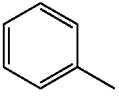 | —CH₃ | —CH₃ |
| C56 | 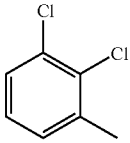 | —CH₃ | H |
| C57 | 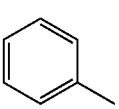 | —C₂H₅ | H |
| C58 | 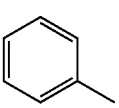 | 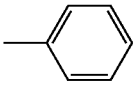 | H |
| C59 | 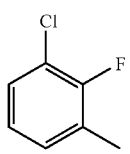 | H | H |
| C60 | 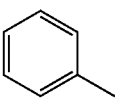 | 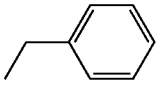 | H |
| C61 | 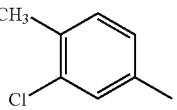 | H | H |

TABLE 1-continued
| Cmpd | Structure | R³ | |
|---|---|---|---|
| C62 | 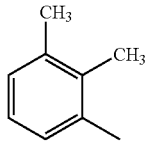 | —CH₃ | H |
| C63 | 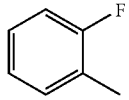 | H | H |
| C64 | 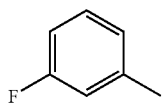 | H | H |
| C65 | 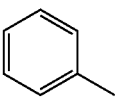 | —CH(CH₃)₂ | H |
| C66 | 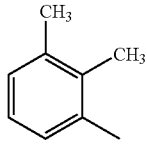 | H | H |
*((1S)-1-phenylethyl) isomer
**((1R)-1-phenylethyl) isomer
Formula I where $R^1$ and $R^2$ are hydrogen and $R^4$ is formula (D):
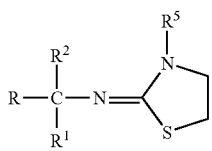
ID
| Cmpd No | R | R⁵ |
|---|---|---|
| D1 | 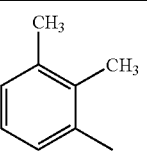 | —COCH₃ |
| D2 | 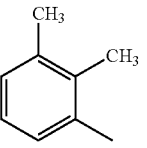 | —SO₂N(CH₃)₂ |
| D3 | 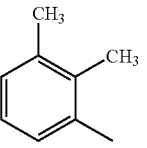 | —PO(OC₂H₅)₂ |
| D4 | 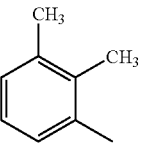 | —PS(OC₂H₅)₂ |

TABLE 1-continued
| D5 | 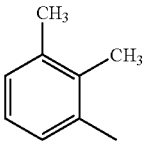 | —CO₂CH₃ |
| D6 | 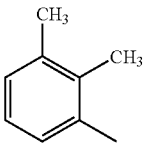 | —CHO |
| D7 | 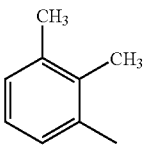 | —CONHCH₃ |
| D8 | 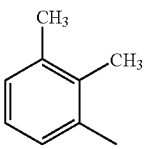 | —CSNHCH₃ |
| D9 | 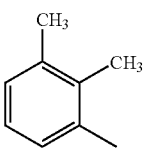 | —CH=NC₂H₅ |
| D10 | 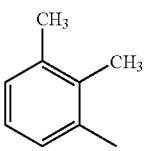 | —CH=NOC₂H₅ |
| D11 | 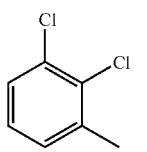 | —COCH₃ |
| D12 | 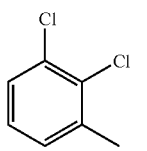 | —SO₂N(CH₃)₂ |
| D13 | 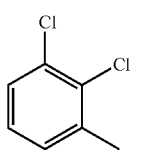 | —PO(OC₂H₅)₂ |
| D14 | 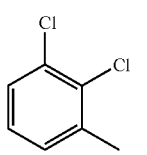 | —PS(OC₂H₅)₂ |

TABLE 1-continued

| | | |
|---|---|---|
| D15 | 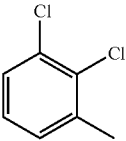 | —CO$_2$CH$_3$ |
| D16 | 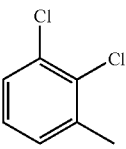 | —CHO |
| D17 | 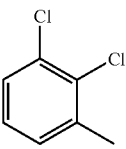 | —CONHCH$_3$ |
| D18 | 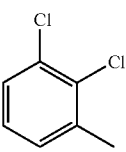 | —CSNHCH$_3$ |
| D19 | 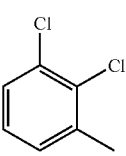 | —CH=NC$_2$H$_5$ |
| D20 | 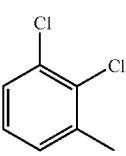 | —CH=NOC$_2$H$_5$ |
| D21 | 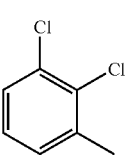 | —PS(OCH$_3$)$_2$ |

The following table sets forth physical characterizing data for certain compounds of formula I of the present invention:

TABLE 2

Insecticidal Benzylamino Heterocyclic Derivatives Compound Characterization

| | Molecular Formula | Melting Point (° C.) of Solids Or Physical State |
|---|---|---|
| A1 | C$_{10}$H$_{10}$Cl$_2$N$_2$O | 113-115 |
| A2 | C$_{10}$H$_{11}$ClN$_2$O | OIL |
| A3 | C$_{10}$H$_{11}$ClN$_2$O | OIL |
| A4 | C$_{10}$H$_{11}$ClN$_2$O | 86-88 |
| A5 | C$_{10}$H$_{10}$Cl$_2$N$_2$O | OIL |
| A6 | C$_{10}$H$_{10}$Cl$_2$N$_2$O | 121-124 |
| A7 | C$_{10}$H$_{10}$Cl$_2$N$_2$O | OIL |
| A8 | C$_{10}$H$_{10}$Cl$_2$N$_2$O | 102-105 |
| A9 | C$_{11}$H$_{11}$F$_3$N$_2$O | 78-79 |
| A10 | C$_{11}$H$_{11}$F$_3$N$_2$O | OIL |
| A11 | C$_{11}$H$_{11}$F$_3$N$_2$O | 114-115 |
| A12 | C$_{11}$H$_{14}$N$_2$O$_2$ | OIL |
| A13 | C$_{12}$H$_{16}$N$_2$O$_3$ | OIL |
| A14 | C$_{12}$H$_{16}$N$_2$O$_3$ | OIL |
| A15 | C$_{12}$H$_{16}$N$_2$O$_3$ | SOLID |
| A16 | C$_{12}$H$_{16}$N$_2$O$_3$ | SOLID |
| A17 | C$_{12}$H$_{16}$N$_2$O$_3$ | 108-112 |
| A18 | C$_{11}$H$_{14}$N$_2$O$_2$ | 99-102 |
| A19 | C$_{11}$H$_{14}$N$_2$O$_2$ | 75-78 |
| A20 | C$_{12}$H$_{16}$N$_2$O$_3$ | OIL |
| A21 | C$_{11}$H$_{14}$N$_2$O | OIL |
| A22 | C$_{12}$H$_{16}$N$_2$O | OIL |
| A23 | C$_{12}$H$_{16}$N$_2$O | OIL |
| A24 | C$_{11}$H$_{14}$N$_2$O | OIL |
| A25 | C$_{12}$H$_{16}$N$_2$O | 81-83 |
| A26 | C$_{12}$H$_{16}$N$_2$O | 85-88 |
| A27 | C$_{12}$H$_{16}$N$_2$O | OIL |

TABLE 2-continued

Insecticidal Benzylamino Heterocyclic Derivatives Compound Characterization

| | Molecular Formula | Melting Point (° C.) of Solids Or Physical State |
|---|---|---|
| A28 | $C_{10}H_{12}N_2O$ | OIL |
| A29 | $C_{11}H_{14}N_2O$ | OIL |
| A30 | $C_{11}H_{13}ClN_2O$ | 100-102 |
| A52 | $C_{11}H_{14}N_2O$ | 110-112 |
| A53 | $C_{12}H_{16}N_2O$ | 129-133 |
| A54 | $C_{11}H_{13}ClN_2O$ | 104-108 |
| A55 | $C_{11}H_{13}ClN_2O$ | 98-102 |
| A56 | $C_{11}H_{13}ClN_2O$ | OIL |
| A57 | $C_{11}H_{14}N_2O$ | OIL |
| A58 | $C_{11}H_{14}N_2O$ | SOLID |
| A59 | $C_{12}H_{16}N_2O$ | OIL |
| A60 | $C_{12}H_{16}N_2O$ | OIL |
| A61 | $C_{11}H_{14}N_2O$ | 81-83 |
| A62 | $C_{11}H_{12}Cl_2N_2O$ | 100-105 |
| A63 | $C_{12}H_{16}N_2O$ | 116-119 |
| A64 | $C_{16}H_{16}N_2O$ | 151-153 |
| A65 | $C_{10}H_{10}ClFN_2O$ | 42-45 |
| A66 | $C_{17}H_{18}N_2O$ | 129-131 |
| A67 | $C_{11}H_{13}ClN_2O$ | 130-131 |
| A68 | $C_{11}H_{13}ClN_2O$ | 63-65 |
| A69 | $C_{13}H_{18}N_2O$ | 149-151 |
| A70 | $C_{12}H_{16}N_2O$ | 48-50 |
| A71 | $C_{10}H_{11}FN_2O$ | OIL |
| A72 | $C_{11}H_{13}FN_2O$ | 132-135 |
| A73 | $C_{11}H_{13}FN_2O$ | 104-106 |
| A74 | $C_{16}H_{16}N_2O$ | 143-148 |
| A75 | $C_{14}H_{14}N_2O$ | 96-100 |
| A76 | $C_{10}H_{11}FN_2O$ | OIL |
| A77 | $C_{11}H_{11}F_3N_2O$ | 165-167 |
| A78 | $C_{11}H_{14}N_2O_2$ | OIL |
| A79 | $C_{12}H_{13}F_3N_2O$ | 139-142 |
| B1 | $C_{16}H_{25}N_2O_3PS$ | OIL |
| B2 | $C_{14}H_{18}N_2O_2$ | 125-126 |
| B3 | $C_{13}H_{18}N_2O_3S$ | 127-128 |
| B4 | $C_{14}H_{21}N_2O_3PS$ | OIL |
| B5 | $C_{18}H_{26}N_2O_3$ | OIL |
| B6 | $C_{15}H_{21}N_3O_2$ | OIL |
| B7 | $C_{15}H_{20}N_2O_2$ | 85-86 |
| B8 | $C_{14}H_{21}N_3O_3S$ | OIL |
| B9 | $C_{14}H_{19}N_3O_2$ | 135-136 |
| B10 | $C_{16}H_{25}N_2O_4P$ | OIL |
| B11 | $C_{15}H_{20}N_2O_3$ | 109-110 |
| B12 | $C_{14}H_{18}N_2O_3$ | 119-120 |
| B13 | $C_{14}H_{21}N_2O_4P$ | OIL |
| B14 | $C_{16}H_{27}N_4O_2P$ | OIL |
| B15 | $C_{15}H_{22}N_2O_2$ | OIL |
| B17 | $C_{14}H_{19}N_3OS$ | 122-123 |
| B31 | $C_{13}H_{15}N_3O$ | 125-127 |
| B32 | $C_{20}H_{24}N_2O_2$ | OIL |
| B33 | $C_{15}H_{22}ClN_2O_3PS$ | OIL |
| B34 | $C_{15}H_{24}ClN_4O_2P$ | OIL |
| B35 | $C_{13}H_{18}ClN_2O_3PS$ | 94-95 |
| B36 | $C_{12}H_{12}ClN_3O$ | 126-127 |
| B37 | $C_{13}H_{16}ClN_3OS$ | SOLID |
| B38 | $C_{13}H_{15}ClN_2O_2$ | SOLID |
| B39 | $C_{14}H_{17}ClN_2O_2$ | SOLID |
| B40 | $C_{16}H_{23}N_3OS$ | 127-128 |
| B41 | $C_{15}H_{21}N_3OS$ | 127-128 |
| B42 | $C_{13}H_{16}FN_3OS$ | OIL |
| B43 | $C_{13}H_{16}FN_3OS$ | OIL |
| B44 | $C_{13}H_{16}FN_3OS$ | OIL |
| B45 | $C_{18}H_{19}N_3OS$ | 123-128 |
| B46 | $C_{13}H_{17}N_3OS$ | 109-112 |
| B47 | $C_{16}H_{17}N_3OS$ | 136-140 |
| B48 | $C_{13}H_{14}F_3N_3OS$ | OIL |
| B49 | $C_{14}H_{19}N_3OS$ | OIL |
| C1 | $C_{11}H_{14}N_2S$ | OIL |
| C2 | $C_{10}H_{12}N_2S$ | 82 |
| C3 | $C_{10}H_{13}N_2S \cdot I$ | SOLID |
| C4 | $C_{10}H_{11}Cl_2N_2S \cdot Cl$ | 164-166 |
| C5 | $C_{10}H_{13}N_2S \cdot Cl$ | 100-102 |
| C6 | $C_{10}H_{12}ClN_2S \cdot Cl$ | 187-188 |
| C7 | $C_{10}H_{11}Cl_2N_2S \cdot Cl$ | 218-220 |
| C8 | $C_{11}H_{14}N_2S$ | 94-96 |
| C9 | $C_{10}H_{10}Cl_2N_2S$ | 119-121 |
| C10 | $C_{11}H_{15}N_2S \cdot Cl$ | 148-150 |
| C11 | $C_{12}H_{17}N_2S \cdot Cl$ | 180-182 |
| C12 | $C_{12}H_{17}N_2S \cdot Cl$ | 146-148 |
| C13 | $C_{12}H_{17}N_2S \cdot Cl$ | 170-173 |
| C14 | $C_{12}H_{16}N_2S$ | 154-155 |
| C15 | $C_{10}H_{12}ClN_2S \cdot Cl$ | 148-150 |
| C16 | $C_{10}H_{12}ClN_2S \cdot Cl$ | 145-147 |
| C17 | $C_{10}H_{11}Cl_2N_2S \cdot Cl$ | 163-165 |
| C18 | $C_{10}H_{11}Cl_2N_2S \cdot Cl$ | 212-213 |
| C19 | $C_{10}H_{11}Cl_2N_2S \cdot Cl$ | 202-204 |
| C20 | $C_{11}H_{12}F_3N_2S \cdot Cl$ | 192-194 |
| C21 | $C_{11}H_{12}F_3N_2S \cdot Cl$ | 147-148 |
| C22 | $C_{11}H_{12}F_3N_2S \cdot Cl$ | 129-131 |
| C23 | $C_{11}H_{15}N_2OS \cdot Cl$ | 118-120 |
| C24 | $C_{11}H_{15}N_2OS \cdot Cl$ | 128-130 |
| C25 | $C_{12}H_{16}N_2O_2S$ | 82-85 |
| C26 | $C_{10}H_{11}FN_2S$ | SOLID |
| C27 | $C_{11}H_{13}ClN_2S$ | 124-125 |
| C49 | $C_{11}H_{14}N_2S$ | 110-113 |
| C50 | $C_{11}H_{13}ClN_2S$ | 118-120 |
| C51 | $C_{11}H_{13}ClN_2S$ | 134-135 |
| C52 | $C_{11}H_{13}ClN_2S$ | OIL |
| C53 | $C_{14}H_{18}N_2O_2S$ | LIQUID |
| C54 | $C_{11}H_{14}N_2S$ | 84-86 |
| C55 | $C_{12}H_{16}N_2S$ | OIL |
| C56 | $C_{11}H_{12}Cl_2N_2S$ | 114-116 |
| C57 | $C_{12}H_{16}N_2S$ | 105-106 |
| C58 | $C_{16}H_{16}N_2S$ | 124-126 |
| C59 | $C_{10}H_{10}ClFN_2S$ | 92-94 |
| C60 | $C_{17}H_{18}N_2S$ | 122-123 |
| C61 | $C_{11}H_{13}ClN_2S$ | 90-95 |
| C62 | $C_{13}H_{18}N_2S$ | 120-121 |
| C63 | $C_{10}H_{11}FN_2S$ | 106-109 |
| C64 | $C_{10}H_{11}FN_2S$ | SOLID |
| C65 | $C_{13}H_{18}N_2S$ | 110-114 |
| C66 | $C_{12}H_{16}N_2S$ | 110-114 |
| D2 | $C_{14}H_{21}N_3O_2S_2$ | 81-84 |
| D4 | $C_{16}H_{25}N_2O_2PS_2$ | LIQUID |
| D5 | $C_{14}H_{18}N_2O_2S$ | 129-131 |
| D11 | $C_{12}H_{12}Cl_2N_2OS$ | 137-140 |
| D12 | $C_{12}H_{15}Cl_2N_3O_2S_2$ | 119-120 |
| D14 | $C_{14}H_{19}Cl_2N_2O_2PS_2$ | LIQUID |
| D15 | $C_{12}H_{12}Cl_2N_2OS$ | 105-110 |
| D21 | $C_{12}H_{15}Cl_2N_2O_2PS_2$ | LIQUID |

Candidate insecticides were evaluated for insecticidal activity by observing mortality in a population of treated cotton aphid (*Aphis gossypii*) on cotton plant leaf discs when compared to like populations of untreated cotton aphid on cotton plant leaf discs. These tests were conducted in the following manner:

Three week to one month-old cotton plants (*Gossypium hirsutum*) were prepared for infesting by cutting off the cotyledons and new true leaf growth, leaving the oldest two true leaves. The prepared test plant was infested with cotton aphids by translocation from cotton plants grown in a cotton aphid colony. The wells of clear 128-well trays (CD-International, Pittman, N.J.) were filled with 1 mL of a warm, aqueous 3% agar solution and allowed to cool to ambient temperature. The aphid infested cotton leaves were removed from the plants and placed bottom side up on a cutting platform. Circular discs were cut from the infested leaves and placed bottom side up onto the cooled agar gel, one disc per well. Each leaf disc was visually inspected to assure that a minimum of 10 live aphids were present. A 50 mM stock solution of the test compound was prepared by dissolving the appropriate amount of the test compound in DMSO. A solution comprising 1000 part per million (ppm) of each test compound was prepared by dissolving 10 μl of the stock solution in 140 μl of an aqueous 0.003% Kinetic® (a nonionic wetter/spreader/penetrant adjuvant, Helena Chemical Company, Collierville, Tenn.) solution. If needed, the solution of 1000 ppm of test compound was serially diluted with a solution consisting of 66 mL of DMSO and 30 μl of Kinetic® in 934 mL of water (diluting solution) to provide solutions of each test compound for lower rates of application, for example, 300 ppm, 100 ppm, 30 ppm, or 10 ppm. Each replicate infested test plant disc was sprayed with 10 μl of the test solution at about 8 psi for 1 second. For comparison purposes, a solution of a standard, such as bifenthrin, prepared in a manner analogous to that set forth above, as well as an aqueous solution of 0.003% Kinetic® containing no test compound and the diluting solution containing no test compound were also sprayed onto infested test plant discs. Upon completion of spraying the solutions of test compound, the solution of standard, and the solutions containing no test compound, the plant discs were allowed to dry. Upon completion of drying, the test trays were covered with a plastic film. Three slits were made in the film over each well to allow air into each well. The test trays were placed in a biochamber (25° C., 16 hours light, 8 hours of dark and 35-40% relative humidity) for three days. After this time, each plant disc was assessed for percent mortality caused by the test compound when compared to the population of aphids that was infested onto the test plant discs containing no test compound. A test compound was designated as possessing insecticidal activity (SA) if there was 40% to 75% mortality of cotton aphid on plant discs sprayed with that compound. If there was 75% mortality or greater of the cotton aphid, a test compound was designated as being more insecticidally active (A). If there was 40% mortality or less of the cotton aphid, the test compound was termed as inactive (I).

An assessment of the insecticidal activity at selected rates of application from this test is provided in Table 3. The test compounds of formula I are identified by numbers that correspond to those in Table 1.

grown in 7.6 cm diameter pots were selected for the test. Each test plant was infested with about 120 adult cotton aphids by placing onto each test plant cuttings of leaves from cotton plants grown in a cotton aphid colony. Once infested, the test plants were maintained for up to about 12 hours to allow complete translocation of the aphids onto the test plant. A solution comprising 1000 part per million (ppm) of each test compound was prepared by dissolving 10 milligrams of the test compound in 1 mL of acetone. Each solution was then diluted with 9 mL of a solution of 0.03 mL of polyoxyethylene(10) isooctylphenyl ether in 100 mL of water. About 2.5 mL of solution of each test compound was needed to spray each replicate of test plant (5 mL total for each test compound). If needed, the solution of 1000 ppm of test compound was serially diluted with a solution of 10% acetone and 300 ppm of polyoxyethylene(10) isooctylphenyl ether in water to provide solutions of each test compound for lower rates of application, for example, 300 ppm, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. For comparison purposes, a solution of 10% acetone and 300 ppm of polyoxyethylene(10) isooctylphenyl ether in water containing no test compound was also sprayed onto control test plants. Upon completion of spraying the solutions of test compound and the solution containing no test compound, the plants were allowed to dry. Upon completion of drying, the test and control plants were placed in a tray containing about 2.5 centimeters of water, where they were maintained in a growth chamber for 72 hours. After this time, each plant was assessed for percent mortality caused by the test compound when compared to the population of aphids that was infested onto the test plants prior to treatment with test compound. A test compound was designated as possessing insecticidal activity (SA) if there was 40% to 75% mortality of cotton aphid on plants sprayed with that compound. If there was 75% mortality or greater of the cotton aphid, a test compound was designated as being

TABLE 3

The Following Compounds Of The Present Invention Reduced The Population Of Cotton Aphid By 40 to 100% When Applied At An Application Rate Of 1000 ppm Or Less To Infested Cotton Leaf Discs

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| A2 | A3 | A4 | A5 | A6 | A7 | A8 | A10 | A11 | A12 |
| A13 | A14 | A15 | A16 | A17 | A18 | A19 | A20 | A21 | A22 |
| A23 | A24 | A26 | A27 | A53 | A54 | A79 | B3 | B8 | B11 |
| B12 | B13 | B15 | B40 | B41 | C1 | C3 | C4 | C7 | C8 |
| C9 | C12 | C13 | C14 | C16 | C17 | C19 | C20 | C21 | C22 |
| C23 | C24 | C25 | C27 | C50 | C52 | C53 | C65 | C66 | D2 |
| D4 | D5 | D12 | D14 | D15 | | | | | |

Candidate insecticides were evaluated for insecticidal activity by observing mortality in a population of cotton aphid (*Aphis gossypii*) on treated cotton plants when compared to like populations of cotton aphid on untreated plants. These tests were conducted in the following manner:

For each rate of application of test compound, two seven- to-ten days old cotton seedlings (*Gossypium hirsutium*)

more insecticidally active (A). If there was 40% mortality or less of the cotton aphid, the test compound was termed as inactive (I).

An assessment of the insecticidal activity at selected rates of application from this test is provided in Table 3A. The test compounds of formula I are identified by numbers that correspond to those in Table 1.

TABLE 3A

The Following Compounds Of The Present Invention Reduced The Population Of Cotton Aphid (*Aphis gossypii*) Between 40% and 100% When Applied At An Application Rate Of 1000 ppm Or Less On Infested Cotton Plants

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| A1 | A9 | A25 | A28 | A29 | A30 | A52 | A55 | A56 | A57 |
| A58 | A59 | A60 | A61 | A62 | A63 | A64 | A65 | A66 | A67 |
| A68 | A69 | A70 | A71 | A72 | A73 | A74 | A75 | A76 | A77 |
| A78 | B1 | B2 | B4 | B5 | B6 | B7 | B9 | B10 | B14 |
| B17 | B31 | B32 | B33 | B34 | B35 | B36 | B37 | B38 | B39 |
| B42 | B43 | B44 | B45 | B46 | B47 | B48 | B49 | C2 | C5 |
| C6 | C10 | C11 | C15 | C18 | C26 | C49 | C51 | C54 | C55 |
| C56 | C57 | C58 | C59 | C60 | C61 | C62 | C63 | C64 | D11 |
| D21 | | | | | | | | | |

As set forth in Tables 3 and 3A, the tested compounds of the present invention reduced the aphid population by at least 40% at an application rate of 1000 ppm or less.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An insecticidal composition comprising at least one compound of formula IA

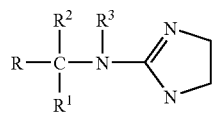
IA where
R is 2,3-dichlorophenyl or 2,3-dimethylphenyl;
$R^1$ is hydrogen or methyl; and
$R^2$ and $R^3$ are hydrogen.

2. An insecticidal composition as claimed in claim 1 further comprising one or more additional compounds selected from the group consisting of pesticides, plant growth regulators, fertilizers and soil conditioners.

3. A method of controlling insects, comprising applying a composition of claim 1 to a locus where insects are present or are expected to be present.

4. An insecticidal composition comprising a compound of formula IG:

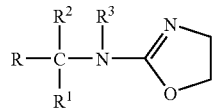
IG wherein
R is selected from 1-naphthyl, phenyl or phenyl optionally substituted with one or two substituents selected from halogen, $(C_1-C_2)$ alkyl, $(C_1-C_2)$ alkoxy, $(C_1-C_2)$ haloalkyl and phenyl;

$R^1$ is selected from hydrogen, $(C_1-C_2)$ alkyl, $(C_1-C_2)$ hydroxyalkyl and $(C_1-C_2)$ haloalkyl;
$R^2$ is selected from hydrogen and $(C_1-C_2)$ alkyl; and
$R^3$ is selected from hydrogen, $(C_1-C_2)$ alkyl,

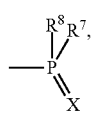 (1)

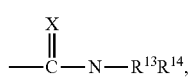 (5)

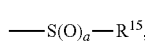 (6)

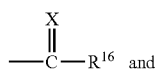 (7)

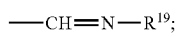 (9)

where
X is oxygen or sulfur;
$R^7$ and $R^8$ are $(C_1-C_2)$ alkoxy;
$R^{13}$ is $(C_1-C_2)$ alkyl;
$R^{14}$ is hydrogen;
a is 2;
$R^{15}$ is $(C_1-C_2)$ dialkylamino;
$R^{16}$ is hydrogen, $(C_1-C_2)$ alkyl or $(C_1-C_2)$ alkoxy; and
$R^{19}$ is $(C_1-C_2)$ alkyl or $(C_1-C_2)$ alkoxy; and
agriculturally acceptable salts thereof;
provided that
when $R^1$ is methyl and $R^2$ and $R^3$ are hydrogen, then R is other than phenyl or phenyl substituted with $(C_1-C_2)$ alkyl;
when R is 1-naphthyl and $R^3$ is hydrogen, then $R^1$ and $R^2$ are other than $(C_1-C_2)$ alkyl; and
when $R^1$, $R^2$ and $R^3$ are hydrogen, then R is other phenyl substituted with one substituent selected from halogen, $(C_1-C_2)$ alkyl and $(C_1-C_2)$ haloalkyl or with two substituents selected from halogen.

5. The insecticidal composition according to claim 4, further comprising one or more additional compounds selected from the group consisting of pesticides, plant growth regulators, fertilizers and soil conditioners.

* * * * *

UNITED STATES PATENT AND TRADEMARK OFFICE
CERTIFICATE OF CORRECTION

PATENT NO. : 8,193,118 B2
APPLICATION NO. : 11/914526
DATED : June 5, 2012
INVENTOR(S) : John A. Dixson et al.

Page 1 of 1

It is certified that error appears in the above-identified patent and that said Letters Patent is hereby corrected as shown below:

Column 73, line 35, change " 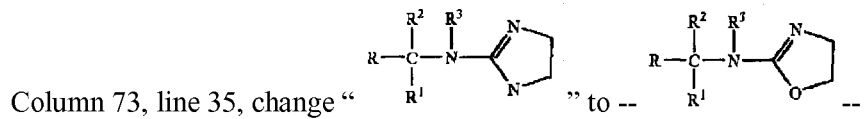 " to --  --

Column 74, line 56, after "R is other" insert --than--

Signed and Sealed this
Eighth Day of January, 2013

David J. Kappos
*Director of the United States Patent and Trademark Office*